United States Patent [19]

Daneshvar

[11] Patent Number: 5,728,066
[45] Date of Patent: Mar. 17, 1998

[54] INJECTION SYSTEMS AND METHODS

[76] Inventor: Yousef Daneshvar, 21459 Woodfarm, Northville, Mich. 48167

[21] Appl. No.: 763,033

[22] Filed: Dec. 10, 1996

Related U.S. Application Data

[60] Provisional application No. 60/008,650, Dec. 13, 1995.
[51] Int. Cl.$^6$ .................................................. A61M 29/00
[52] U.S. Cl. ........................... 604/96; 604/113; 606/194
[58] Field of Search ........................ 604/96, 97, 98, 604/101, 113, 114, 280, 247, 49, 50; 606/192–194, 27, 28

[56] References Cited

U.S. PATENT DOCUMENTS

| | | | |
|---|---|---|---|
| 5,486,192 | 1/1996 | Walinsky | 606/194 |
| 5,533,969 | 7/1996 | Mulder | 604/96 X |
| 5,549,559 | 8/1996 | Eshel | 604/113 |
| 5,556,412 | 9/1996 | Hill | 604/96 X |

*Primary Examiner*—John D. Yasko

[57] ABSTRACT

This application deals with the problem of injection of a therapeutic or procedural fluids into a vascular system and particularly into the arteries. Commonly, these materials will be washed out quickly due to the rush of the blood in the lumen of the vessel and this prevents the best outcome to be achieved. To prevent this problem the applicant introduces a series of catheters and sheaths that allow a resistance mean or a barrier mean to be created in front of the flow of the blood in the lumen of the vessel. So that the speed of the flow of the blood in the vessel will decrease and this prevents from the quick washout of the injected materials from the injected space. In the prototype model this unit the resistance mean is an inflatable balloon that is located on the body of the catheter and the inflation of that balloon will cause the resistance to build up. In order to be able to chose the area of the resistance mean as well as the type of the catheter that can be used with these units a new series of sheaths with resistance means on them are introduced in this application that allows different catheters to be used with them. In another model the balloon will be placed around or next to the catheter and it will cause the resistance to build up. Furthermore this application introduces an injection catheter which has a thermistor in its body and it allows the flow of the fluid to be done in the arterial system. The barriers or the resistance unit of these catheters will prevent the therapeutic or procedural materials that are injected into the area to leave the injected space quickly. Also importantly, the resistance can be used to build a relatively higher pressure in the injected space in order to inject the medication into the closed vessel more forcefully.

20 Claims, 12 Drawing Sheets

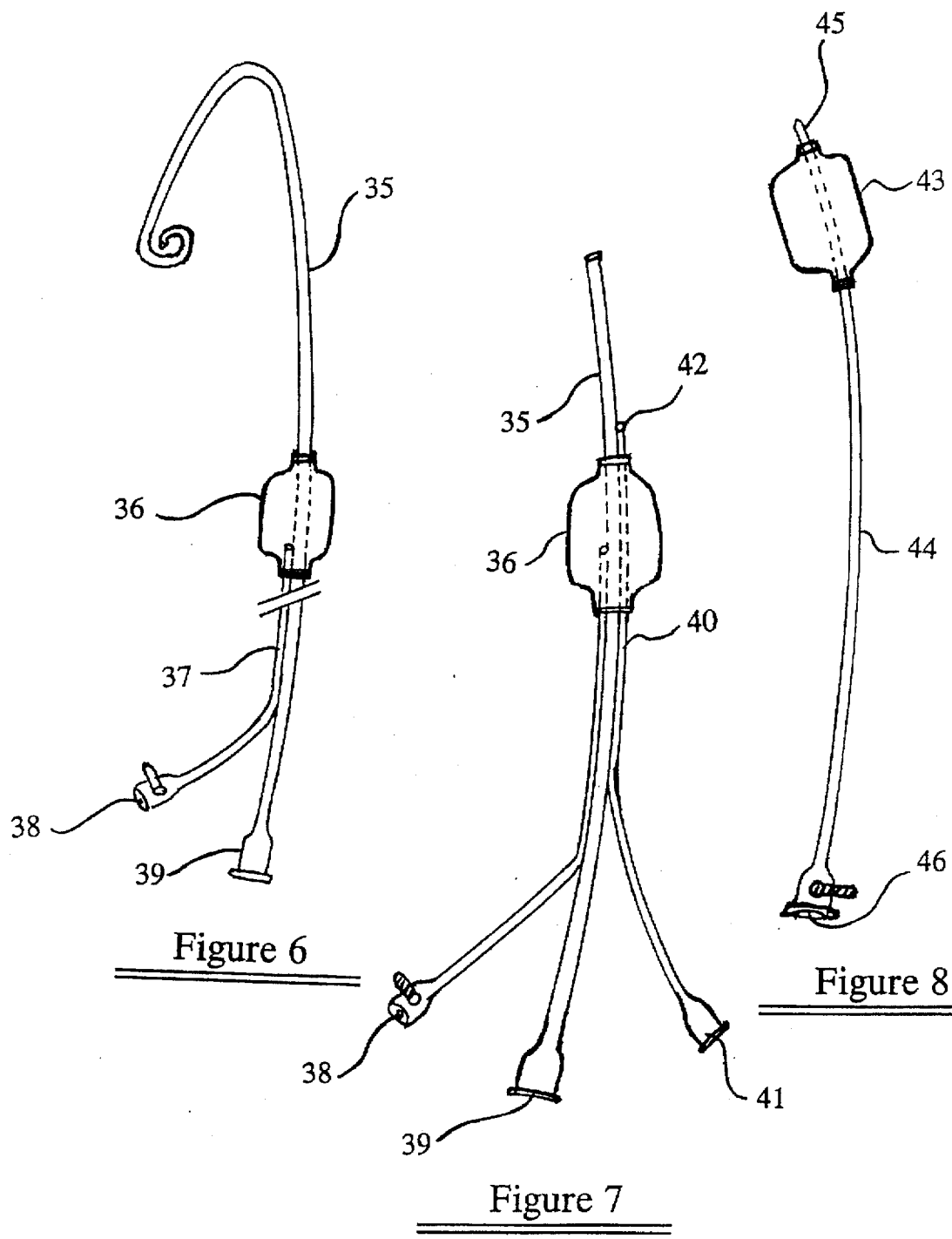

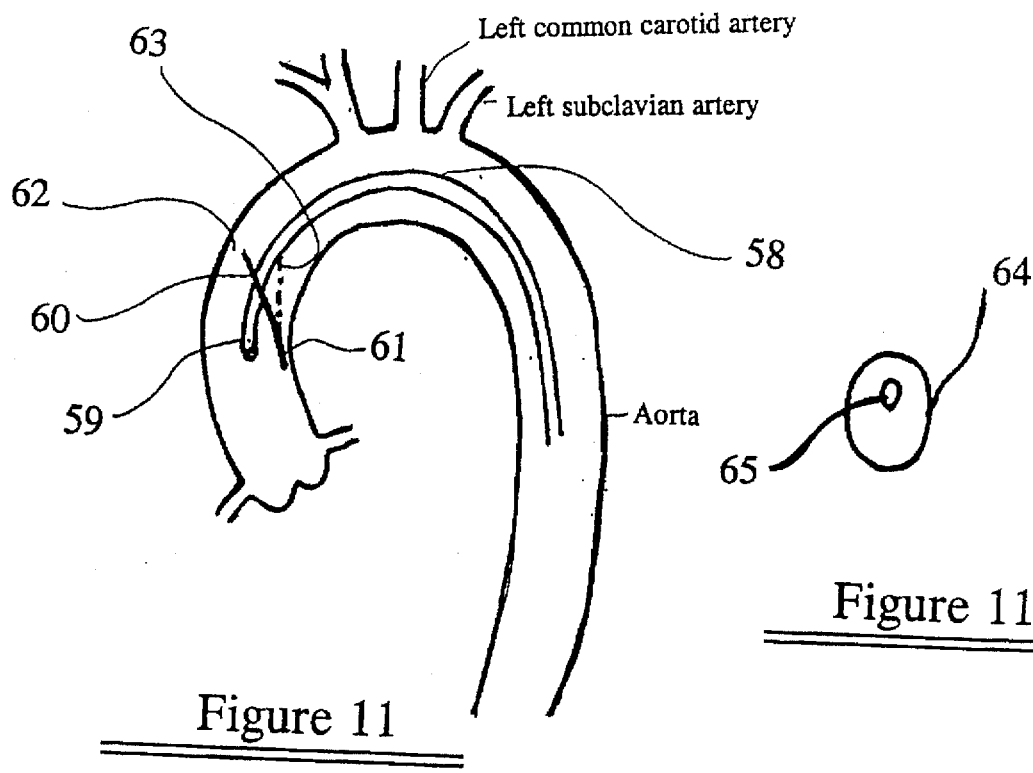
Figure 11
Figure 11A
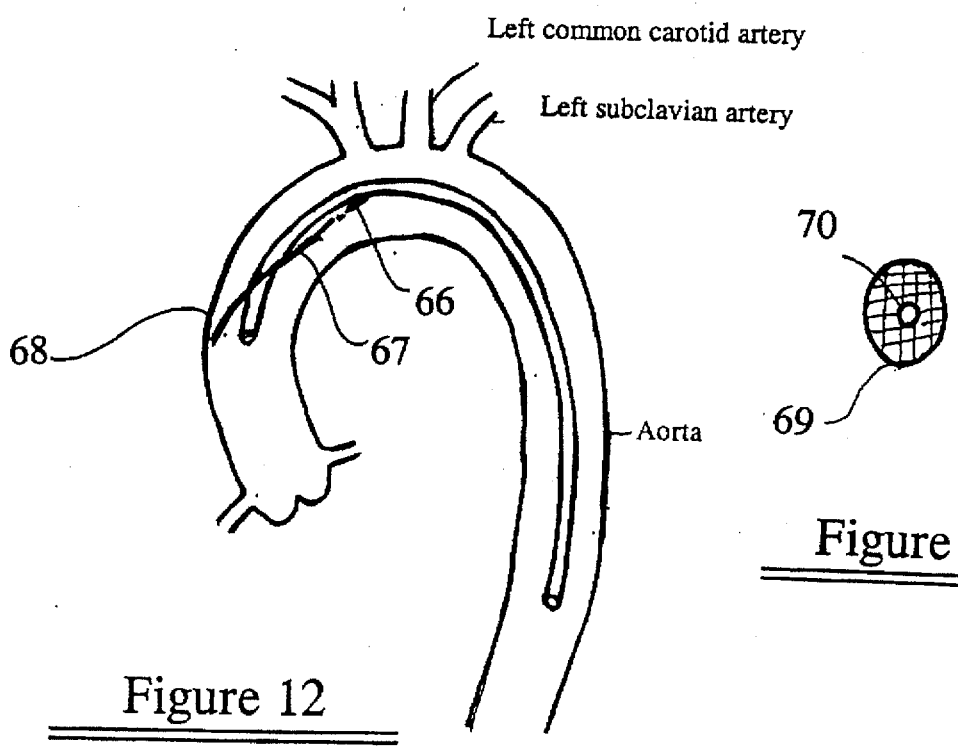
Figure 12
Figure 12A 5,728,066

INJECTION SYSTEMS AND METHODS

REFERENCE TO RELATED APPLICATIONS

This application claims the priorities of Provisional Application No. 60/008,650, filed Dec. 13, 1995, and Regular Application No. 08/512,098, filed Aug. 7, 1995.

BACKGROUND OF THE INVENTION

This application deals with the problem of injection of a therapeutic or procedural fluids into a vascular system and particularly into the arteries. During such an injection commonly the injected material is quickly washed out by the flow of the blood and therefore it does not give a chance to the observer and see the details of the area after the injection of the contrast media. For this reason this applicant previously introduced a series of catheters that had resistance means in their bodies so that the resistance means prevent from the injected fluid to be washed out quickly. However since the size of the aorta is not the same in different people the applicant introduced this model that allows the place that the resistance can be placed to be chosen. This invention also allows to increase the pressure in the injected space in order to force the flow of the medication into an occluded vessel. Furthermore the application considers introduces a series of catheters and methods that allow an easier injection of the procedural or the therapeutic materials into the culprit arteries or a space to be done. Also this application deals with the problem of measuring the blood flow in the arterial system which is very important but difficult and introduces catheters which allows such measurements to be done more accurately. Also importantly, the applicant considers the problem of scratching and scraping the aortic wall during use of large catheters or sheaths and to prevent this he introduces a guidewire with a balloon that will be used during insertion period.

BRIEF EXPLANATION OF INVENTION

This application also deals with a series of catheters which have a barrier means or resistance means on their bodies and resist the flow of the blood in the vessel and therefore prevents from a quick washout of the injected materials from the injected space. The prototype model of these units uses an inflatable balloon that is located on the body of the catheter and allows the inflation of that balloon to be used to cause the resistance to build up inside the vessel. In another model the balloon will be placed around or next to the catheter and it will cause the resistance to build up. Furthermore this application introduces an injection catheter which has a thermistor in its body and allow the flow of the fluid to be calculated in the arterial system. The barriers or the resistance unit of these catheters prevent the therapeutic or procedural materials that are injected into the area to leave the injected space quickly. Also importantly, the resistance can be used to build a relatively higher pressure in the injected space in order to inject the medication into the closed vessel more forcefully.

This application also combines those factors with specially shaped catheters as was presented in the previous application of this applicant which allows a selective injection into the openings of certain vessels to be done. These catheters will be made from a polymer and a mesh of metal very similar to the commonly used cardiac catheters or any of the state of the art cardiac catheters that can be made to allow them to be placed in selective areas of the aorta almost automatically. The design of these units allows the delivery of different diagnostic or therapeutic materials into certain vessels to occur. These catheters have a design and construction that will make such a placement possible. For such a purpose the catheter's curvature is designed to make the body of the catheter to touch the wall of the aorta in a particular area and to bend and move in a favorable direction to end up in the desired area or opening. These are part of prior art that is available now and will be used with the improvements introduced in these catheters. This applicant also considers the his right for the methods for the development of various resistance units as well as the methods of measuring the flow of the blood in the arterial system.

FIGURES

Please notice that many of the options, or different parts or important embodiments mentioned in these figures are to be shared by all of the units mentioned in this applications if applicable.

BRIEF EXPLANATION OF THE FIGURES

Please notice that FIGS. 1–8 and 15 deals with the main idea of this invention. FIGS. 9–12A shows different types of resistant units and FIGS. 13 and 14 shows how the distal end of these catheters may vary.

FIG. 6 shows a catheter which has a balloon on its body to create resistance against the moving blood.

FIG. 7 shows a balloon enhanced sheath unit which has a tubing that allows the pressure of the distal area to be measured.

FIG. 8 shows a resistance balloon with a torque-able body.

FIG. 9 shows a catheter with two lumen and a wall shaped barrier.

FIG. 10 shows a catheter with a barrier made from a screen to catch particles inside the aorta.

FIG. 11 show a catheter with a wall-shaped barrier.

FIG. 11A shows the from view of the barrier of the catheter which was shown in FIG. 11.

FIG. 12 show a catheter with a wall-shaped barrier except it has different angulation.

FIG. 12A shows the front view of a barrier which is made from screen.

FIG. 13 shows a catheter that has a special tip and is designed to fit the right coronary cusp.

FIG. 14 shows a catheter that is designed to be placed inside or in the left coronary cusp.

DETAILED EXPLANATION OF THE FIGURES

Figure 1:
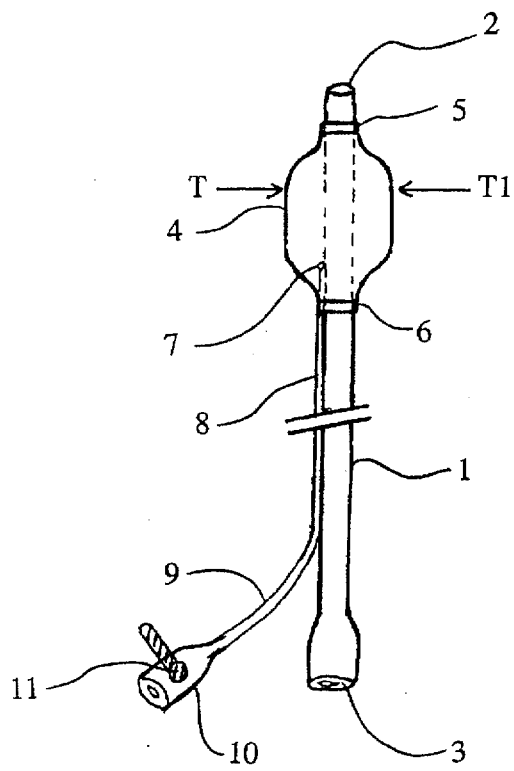
FIG. 1 shows a balloon enhanced sheath unit that allows a catheter to be entered via its lumen.
Figure 15:
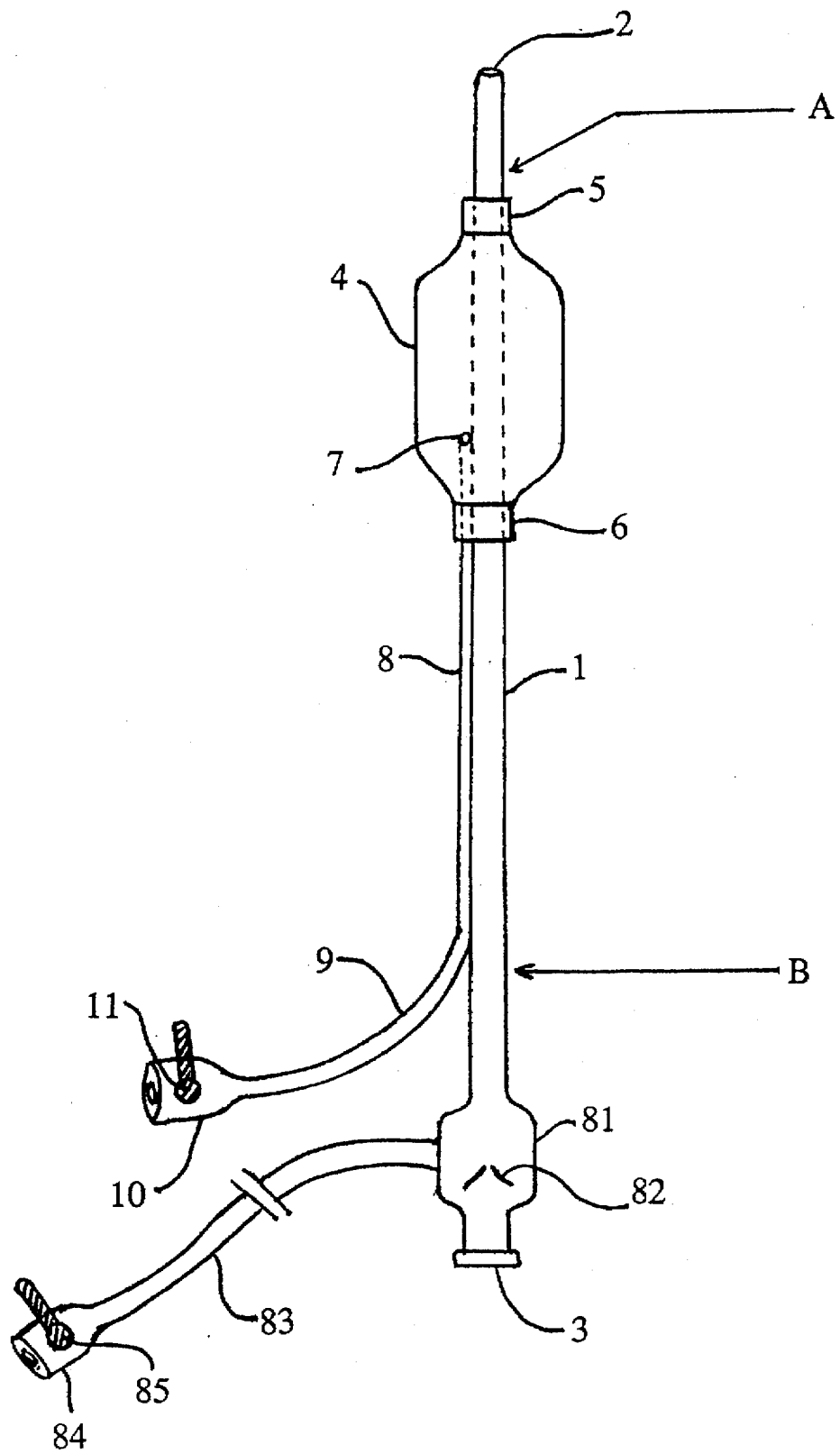
FIG. 15 shows a sheath unit that has an inner valve and an injection port as well.
Figure 16:
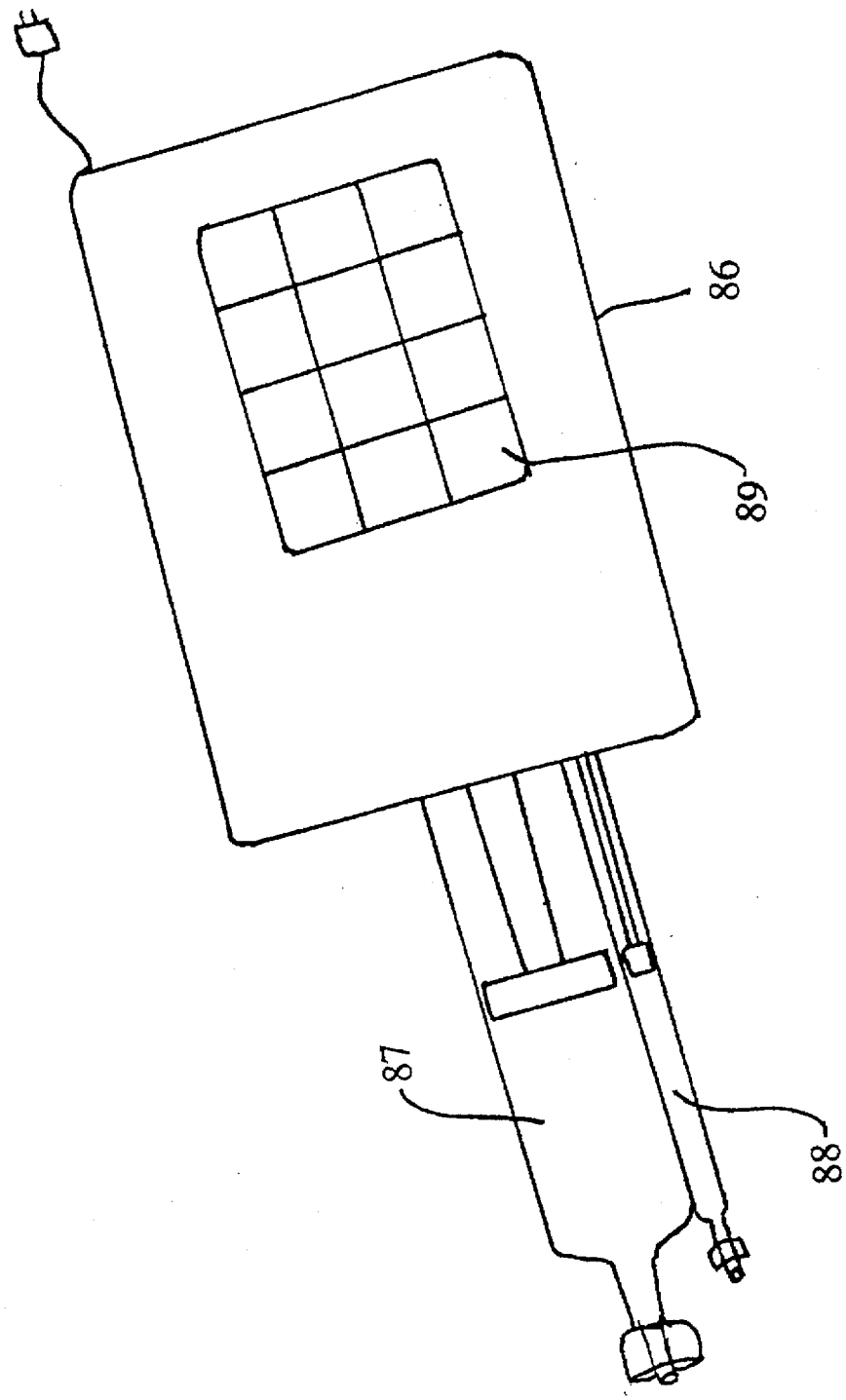
FIG. 16 shows a computerized injection system for use with these models.

FIG. 1 shows schematically a prototype balloon tipped sheath unit that allows a resistance against the flow of the blood in the vascular system to be created (specially in arterial system). Importantly, this unit is to be used in combination with a commonly used injection catheter or a catheter similar to one shown in FIG. 3. This unit has a tubular body as shown at 1 with a distal opening 2 and a proximal opening 3. The opening 3 will have a size and shape to fit the commonly used standard syringes and similar pieces. This unit allows the fluid to move inside this tube for various reasons. The tubular body of this unit will be made from a flexible polymer which may also have some reinforcement such as a lining or a mesh of steel or similar material in order to give more torque and resistance to the body of this unit. This unit has an inflatable balloon as shown schematically at 4 which is fixed on the body of the unit at point 5 and 6. Importantly, in some models that balloon may not be fixed in the body and may be moved to allow its position to be changed as shown at FIG. 15 and the segment between the A and B. At this figure this balloon is shown in inflated condition and when deflated it will be a sheath that can be used easily in patients. This balloon has an inflation tubing such as one shown at 8 and 9 which has an opening inside the balloon as shown at 7 and an inflation port as shown at 10. The inflation port allows a standard syringe or an automatic injection pump system as shown at FIG. 16 to be used for the inflation of the balloon with a gas or a fluid. The valve mean 11 will allow the inflation port to be closed. The body of this unit and balloon may be coated with Heparin or any other anti thrombotic agent in order to eliminate or diminish the chance of adhering the blood particles to the body of this unit.

Importantly, this unit may also use a dilator probe and a J shaped guidewire for placement, which all may be packed with this unit. A model of the dilator probe and J shaped guidewire are shown at FIGS. 2A and 2B and are well known prior arts. All of these plus a needle for puncturing the vessel may be provided in a package in order to allow the insertion of the sheath to the vessel to be done by this complete unit. This package may also have the catheter shown at FIG. 3 as well.

Figure 2:
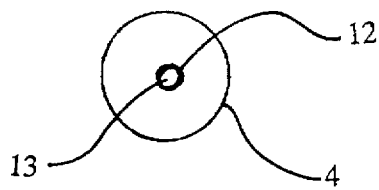
FIG. 2 shows the cross cut of the sheath unit shown in the previous picture.
Figure 2A:
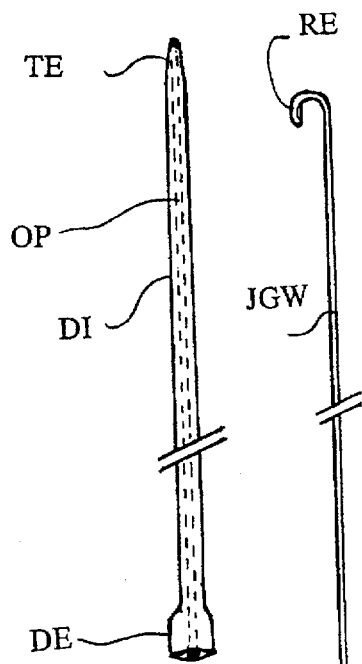
FIG. 2A shows schematically a dilator probe which will be similar to a commonly used dilator piece.
Figure 2B:
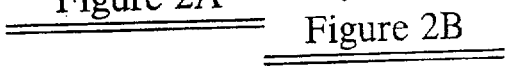
FIG. 2B shows schematically a J shaped spring guidewire similar to commonly used J shaped guidewires.

FIG. 2 shows schematically the cross cut view of the unit shown in the previous FIG. 1 in the area shown at T and T1. In this figure the cross cut of the tubular body of the unit is marked at 12 and the wall of the balloon at 4 and the inner lumen of the unit tube at 13.

FIG. 2A shows schematically a dilator probe which is similar to the commonly used dilator pieces that are used with the intra-vascular sheath units for the dilatation of the area of the wound and the vessel. This is made from a relatively rigid polymer that has a tubular body shown at DI and an internal opening shown at OP, a tapered end shown at TE and a proximal end shown at DE. This may be packed with the unit shown at FIG. 1 as mentioned above.

FIG. 2B shows schematically a J shaped spring guidewire which is very similar to the commonly used J shaped guidewires. These are used in order to be placed via the needle and inside the vessel to allow the dilator and the sheath units to be placed over it. This may be packed with the units shown at FIGS. 1 and 2A. In this figure the body of the guidewire is shown at JGW and the retractable end of this unit at RE.

Figure 3:
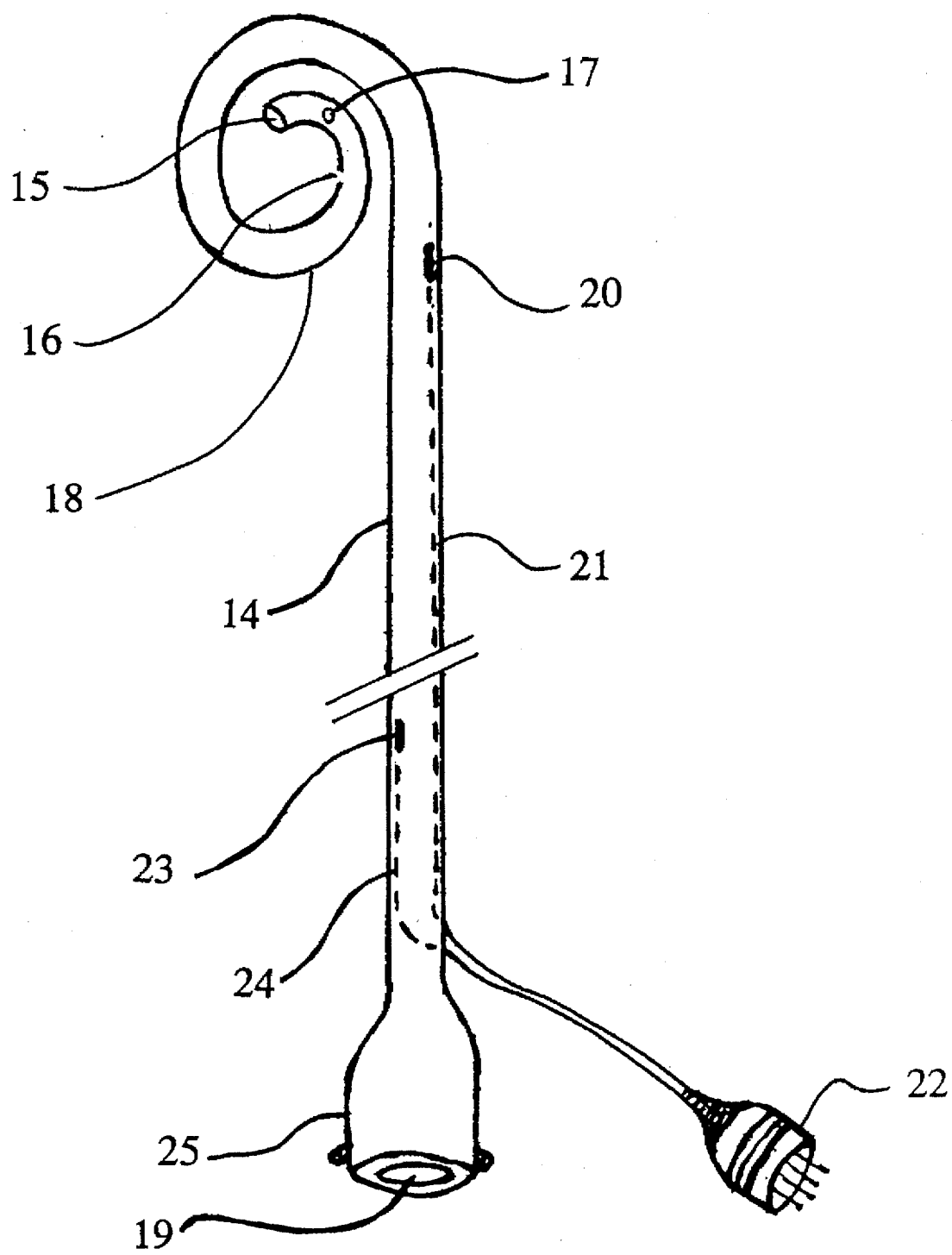
FIG. 3 shows a pig tail catheter which has thermistors in its body to allow the circulation of the blood to be measured.

FIG. 3 shows schematically a special catheter which is designed to be used with the resistance unit shown at FIG. 1. This unit not only allows the injection of fluids inside a vessel of the body to be done but also allows the volume of the fluid pumped out of the heart in one minute (Cardiac Output) to be calculated. Basically this catheter will be made to be similar to the body of a commonly used high quality cardiac catheters that are now available for the injection into the ventricles, the coronary arteries, Aorta and similar places. This unit has a body with a torque and may have a surface coating of Heparin or any other proper anti thrombotic agent in order to diminish the chance of sticking the blood particles to the body of the catheter. This catheter may have different shapes, designs or make ups in its tip although in the prototype model it has a pig tail type shape as shown at 18 in this picture. The tip of the catheter may have opening in its end as shown at 15 as well as side holes as shown at 16 and 17 in order to allow the fluid to move in and out. The body of this unit has a proximal end 19 which allows the communication between the proximal and distal openings of this unit to occur. The unit also has a outer body at the end marked at 25 which will be similar to the body of the commonly used catheters with a female ending that allows the connection between this part and the other incoming units such as the tip of the commonly used manifolds or standard syringes and injection units to occur.

Importantly, besides those properties this catheter has a special unique construction with having at least one thermistors such as one shown at 23 in its body that allows the temperature in the vicinity of the catheter to be verified for computation of the volume of the fluid that goes through that system in a particular time. No 20 shows one of such a thermistors and no 23 shows another thermistor. These thermistors are connected to a jack symbolically shown at 22 by the electrically conductive mean such as wire mean 21 and 24 respectively so that this system allows the change in the temperature of the fluid between these two places to be computed. This capacity adds a significant advantage to this unit since with one catheter and couple injections a very important information about heart function can be calculated as well.

Alternatively, the unit may only have the distal thermistor shown at no 23 which will be connected to the jack 22 by the electrically conductive mean 24. In this case the temperature of the injected fluid can be determined and entered into the computer for calculation by hand or by use of a probe which is will be connected to the computer mean from one side and will be exposed to the injected material from the other side. So that simply this method will allow the temperature of the injected fluid to be checked and then to be compared with the temperature of the fluid which mixes with the blood after injection and by a computer which has the proper hardware and software to perform this calculation. The computer will calculate such a change in temperature by a sophisticated method in order to find the volume of the blood which goes in the area. The probe that allows the computer to sense the temperature of the injected fluid may be similar to the temperature sensitive probe shown at 34 FIG. 4.

At the time of use the catheter 14 will be placed inside the unit shown at FIG. 1 and with use of a guide wire the catheter will be placed in the right area such as inside the left ventricle or the lumen of the aorta in the area which is intended. The balloon enhanced sheath unit shown at FIG. 1 will be positioned in the proper area along the aorta or its branches. At the time which the contrast media or the medication injected into the ventricle or the system the balloon of the unit will be also inflated either by hand or by an automated injection system so that the blockage will occur precisely in the time that it is intended. The deflation time of the balloon and the duration of the inflation all will be decided based on the clinical studies and the intention of use of this method. Importantly, this system allows the modification of the position of the balloon compared to the position of the tip of the catheter and its length. So that the operator will be able to place the balloon in the ascending aorta, the aortic arch or the descending aorta or its branches. This system has an inherited advantage that will be mentioned in this text further.

Importantly, the distance between the place of thermistor and the opening which the injection will be made may vary, this may change based on further research of this model.

Figure 4:
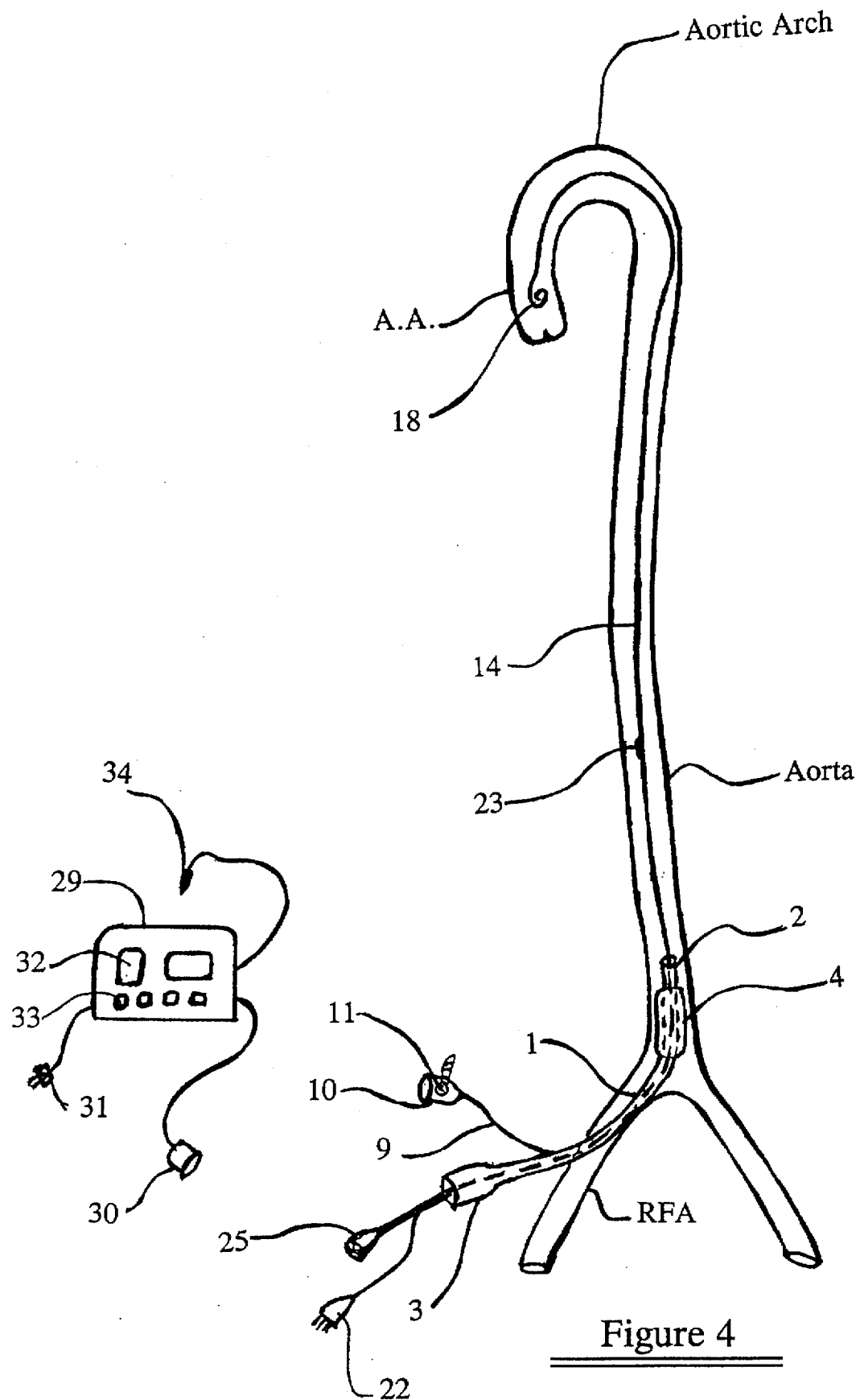
FIG. 4 shows an injection system; a pig tail catheter with a thermistor inside a balloon enhanced sheath unit.

Importantly, the number of the thermistor and the distance between them and the opening which the injection will be made may vary as well in the prototype unit as shown at FIG. 4 the thermistor will be only one thermistor.

FIG. 4 shows schematically a prototype sheath unit such as one shown at FIG. 1 used in combination with an injection catheter similar to one shown at FIG. 3. In this Fig the aorta of a living body is shown with its ascending part marked at A.A. and its arch at A.ARCH and the right femoral artery at RFA. A sheath similar to one shown at FIG. 1 with a short length is placed in the femoral artery. The tubular body of this unit is shown at 1 and its proximal opening at 3 the inflated balloon is shown at 4 and the inflation tubing at 9 as well as the inflation port 10 and the valve mean 11. This unit is inserted into the femoral artery and its tip is placed above the biforcation of the aorta. Also this figure shows the body of a pig tail injection catheter at 14. This catheter has a pig tail tip 18 and it is similar to the catheter shown at FIG. 3 except it has only one thermistor 23. This catheter has a proximal end piece 25 which has standard body similar to the end of similar catheters and allows the unit to be locked to a commonly used manifold. The catheter has the thermistor 23 located in its body which is connected to the jack 22 in order to allow the thermistor to be connected to a computer system for measuring the cardiac output. The computer system is shown symbolically at 29 and it has a matching jack 30 which matches and connects to the jack 22 from the catheter. The jack 31 of this unit allows it to be connected to the electricity of the room. The computer also has a series of indicators one marked at 32 which allows the variables to be seen, it also has a series of control buttons one shown at 33 that allows different functions to be controlled. The computer may also have a probe 34 in order to allow the temperature of the injection solution to be measured for calculation. This kind of computer is part of present art and are available although the programing and the calculations and parameters will be changed to meet this specific need.

This system allows a fluid such as normal saline to be injected into the left ventricle or the lumen of the aorta by the catheter 14 and the temperature of the diluted fluid to be checked by the thermistor 23 located in the body of the catheter and this change to be computed by the computer system 29 to calculate the flow of the blood and measuring the cardiac output. This unit provides the advantage to the commonly used pig tail catheters such as one shown at 14 to allow an important information such as cardiac output of a patient to be measured during cardiac catheterization for various purposes.

Figure 5:
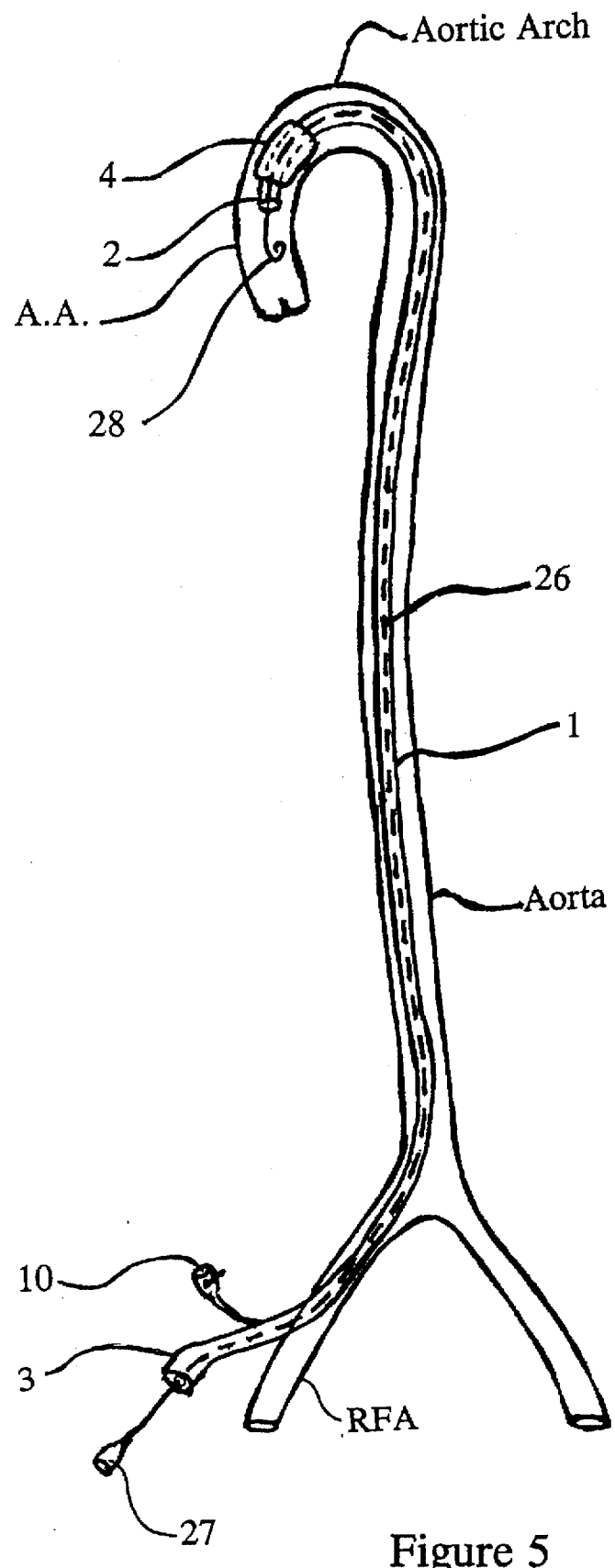
FIG. 5 shows an injection system; a regular pig tail catheter inside a long balloon enhanced sheath unit.

FIG. 5. Shows schematically a combination of a sheath unit such as one shown at FIG. 1 with a regular pig tail injection catheter 26 except this unit has a longer body marked at 1. The purpose of this Fig is to show that the length of the resistance unit may vary in order to allow the resistance unit to be placed in different areas of the aorta for different reasons and producing resistance in different spots of the aorta. In this Fig again the aorta of a living body is shown with the ascending segment marked at A.A., the arch at A.ARCH and the right femoral artery at RFA. The resistance unit has a long tubular body shown at 1 and its proximal opening is shown at 3, the inflated body of the balloon is shown at 4 and the inflation port of the unit at 10. The distal tip of the pig tail catheter is marked at 28 and its body inside the sheath-barrier unit at 26 and its proximal end at 27. This combination allows the injection of the contrast media into the left ventricle or inside the lumen of the aorta to be done and then the mixture of the blood and the contrast media will face the resistance of the balloon and will disperse in the space inside the ventricle and the aorta. However due to the presence of the resistance it has more time to fill the coronary and the coronary bypass grafts with one injection and this will provide much more information than the injection via pig tail catheter alone without the resistance.

FIG. 6 shows schematically a prototype catheter which has the resistance unit as part of its body. This concept was introduced to USPTO office by this applicant in his application of "No delay approach to acute vascular catastrophes". What this unit is; basically consists from one of any of the injection catheters that are available such as for example a commonly used pig tail catheter as shown here at 35 that has a resistance unit here made from an inflatable balloon shown at 36. This balloon has an inflation tubing 37 and an inflation port 38 so that it will allow the balloon to be inflated when the catheter is in its place. The distal end of this catheter is shown at 39 and has a standard catheter ending.

This method allows catheters with different shapes to be made with different sizes and the balloon will be placed in different areas of the catheter's body to be available for particular use.

Importantly, the in some models the balloon may not be fixed on the wall of the catheter in order to allow the position of the balloon on the cath to be adjusted.

FIG. 7 schematically shows a unit similar to the unit shown in the previous FIG. 6 that has a tubing 40 for use for various purposes such as allowing the pressure of the space distal to the balloon to be measured. In this Fig the body of the catheter is shown at 35 and it has the resistance unit symbolically shown as an inflatable balloon (it can be other kinds as well) as shown at 36. This unit has the tubing 40 with its distal opening 42 and its proximal opening 41. Such a system allows the tubing 40 to be used for various reasons such as injection of fluids to the distal space also for the measurement of the pressure of the space distal to resistance.

FIG. 8 this Fig schematically shows how a resistance unit that consist only from a controlable shaft as shown at 44 with a resistance unit shown at 43 and here the resistance unit is made from an inflatable balloon (although it can be other kinds as well) shown at 43. The body of the unit 44 has a contoured soft tip 45 to prevent from damaging the wall of the vessel (it may be made to have a J shaped ending) during the insertion and it has a torque-able resistant body 44 (the degree of the resistance of the body of this unit may vary) and a proximal opening 46 which has a valve as well. This unit will allows it to be placed inside the aorta and next to the injection catheter in order to create a controlable resistance in the tureen of the aorta as explained in the text.

Importantly, the body of this unit may also consist a flexible wire such as a J shaped guide wire.

Importantly, this unit may also have a tubing similar to the tubing 40 from the previous FIG. 7 for various reasons such as the injection of fluids to the area or for measurements of the pressure of the space distal to resistance.

Figure 9:
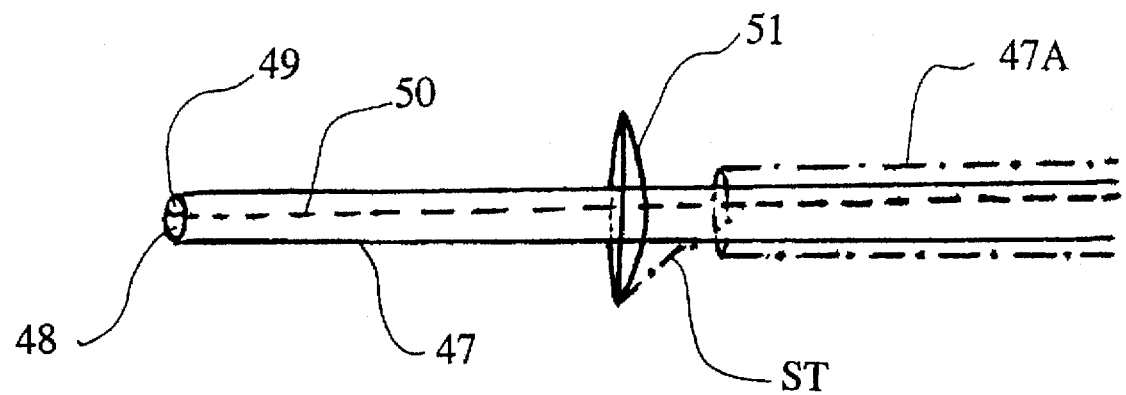

FIG. 9 shows schematically a couple options that the resistance units mentioned in the above figures may have. First. The body of the tubing of the resistance unit=the sheath or the catheter may be made to be a double lumen tubular unit marked at 48 and 49. This will allow various uses for example it will allow one lumen to be used for the injection of the fluid and the other lumen to be used for the placement of a guide wire in order to provide more stiffness and resistance to the body of the combination and to prevent the blood flow to move the resistance away.

Second. This Fig also shows how the barrier part of the resistance unit may be made from a wall as shown in no 51. This wall may be made from a layer of polymer or a fabric that it will function such as an umbrella or a reversed umbrella in order to resist the flow of the blood. In this Fig the body of the catheter is shown at 47, one opening at 48, the other one at 49, and the dividing wall between these two long tubular openings at 50. The dish shaped, barrier is marked at 51. This figure also shows a larger catheter marked at 47A that will function to hold the unit 47 as well as the wall mean 51 inside and will allow them to be delivered to the target area. After the unit is in the proper place then the catheter 47A will be pulled back and out to release the wall mean 51. This figure also shows a string mean ST that is connected to the body of the resistance wall mean 51 in order to allow the position of the wall to be adjusted inside the body.

Figure 10:
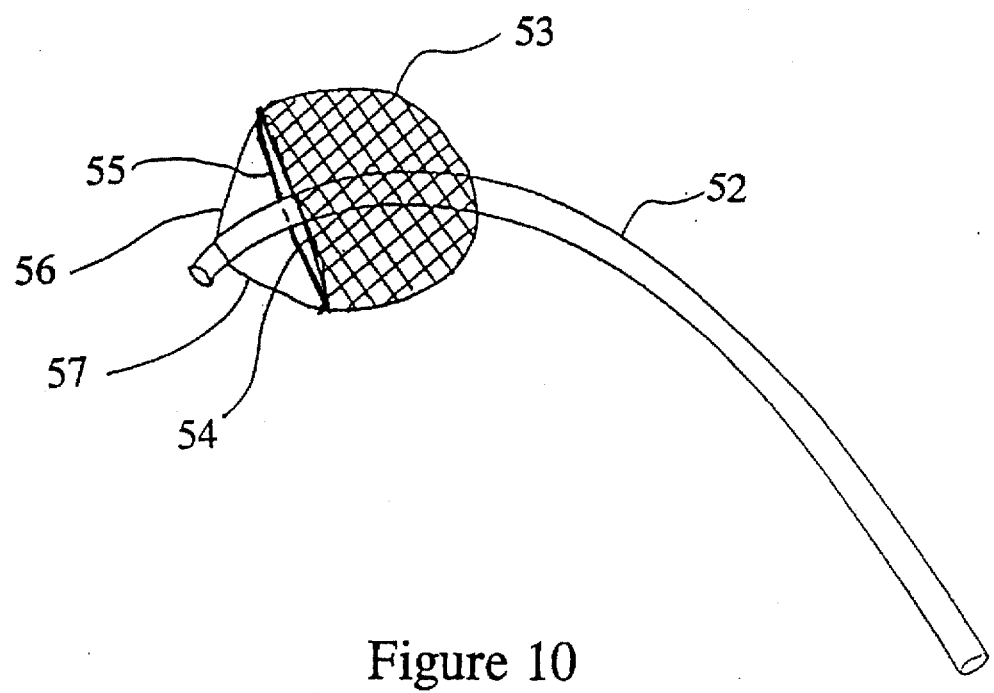

FIG. 10 shows schematically a catheter with a barrier mean that is made from a screen 53 so that it will function like a fish catcher made from a screen. This will be useful to capture the embolic properties which may be released during certain cardiac conditions and interventions. In this model the resistance of the barrier will be low and the screen body of the resistance unit will act like a basket to capture the materials and allow them to be carried out from the site of the approach. This unit will also have fine spring wires 54, 55 in it in order to allow the screen to expand when released. This unit can be released from a larger delivery catheter similar to one shown at 47A FIG. 9 that will hold this unit inside in a compressed form and will allow it to expand when it is out of the covering catheter. In this Fig the body of the tubing is shown at 52, the screen barrier at 53, the spring rim of the barrier is marked at 54, 55. The threads or spring threads that connect the circular spring rim 54, 55 to the body of the catheter are marked at 56 and 57. Importantly, the number of these spring threads may vary. Also, the size, shape and the other important characteristics and properties of this unit may also vary as well.

FIG. 11 shows schematically a catheter with a barrier mean 60 that is made from a wall-shaped unit. This barrier is standing around the tubular body 58 of the catheter which has an open distal end shown at 59. The barrier wall 60 is designed and located on the catheter with an angulation that makes one side of the wall marked at 61 to stand against the wall of the aorta; this will direct the flow of the blood to the other side to move into the area marked at 62 which is open for the blood to escape. This direction will make it possible for the blood to move into bypass grafts that are located in this area and importantly, same kinds of catheters which has barriers placed in different positions will direct blood in different directions in order to allow different vessels or areas of the aorta or the vessel to be studied in more detail. This Fig also shows that the string mean 63 may be connected to the wall mean 61 in order to allow the string to be pulled out or released to change the position of the wall mean. The string mean 63 will be placed inside the lumen or in the wall of the catheter 58 to allow it to be accessible for manipulation. The spring mean 63 may be fixed to the wall of the catheter, or to go through the of the tubing 58 or to go thorough a small tubing in the body of the catheter which is not shown here. The number, position, consistency of the body, location, and all other important characteristics of these strings and the unit as a whole may vary from one model to another.

FIG. 11A schematically shows the from view of the wall mean 60–61 shown in the previous FIG. 11. This figure is to give a general idea about the shape of this wall mean which is like a leaf made from a thin layer and will fit inside the opening of the aorta or a vessel. In this Fig the outer border the wall mean is shown at 64 and the cross cut of the tubing at 65. The size, thickness, consistency of the body, shape, location, and all other important characteristics of these walls and the unit as a whole may vary from one model to another.

FIG. 12 schematically shows a catheter that is very much similar to the one shown in the previous FIG. 11 except in this model the barrier wall mean 67 of this catheter is placed with a different angulation. This is to make the barrier wall mean to stand against the wall of the aorta at 68 and to direct the blood flow to the other side, close to the border 67 which is a different direction than the one shown in FIG. 11.

Importantly, different designs may be chosen as well. This Fig also shows that a string mean 66 similar to the one shown at 63 may be used with this wall mean as well.

FIG. 12A is similar to the previous FIG. 11A. It shows schematically the from view of the wall mean 67–68 shown in the previous FIG. 12. This figure is to give a general idea about the shape of this wall mean that will fit inside the opening of the aorta. However, in this Fig the resistance wall has a screen body in order to prevent the small particle to pass thorough. This will be useful in procedures or conditions that release small particles that may go to the brain and cause a stroke. In this Fig the outer border of the barrier mean is shown at 69 and the cross cut of the tubing at 70.

Figure 13:
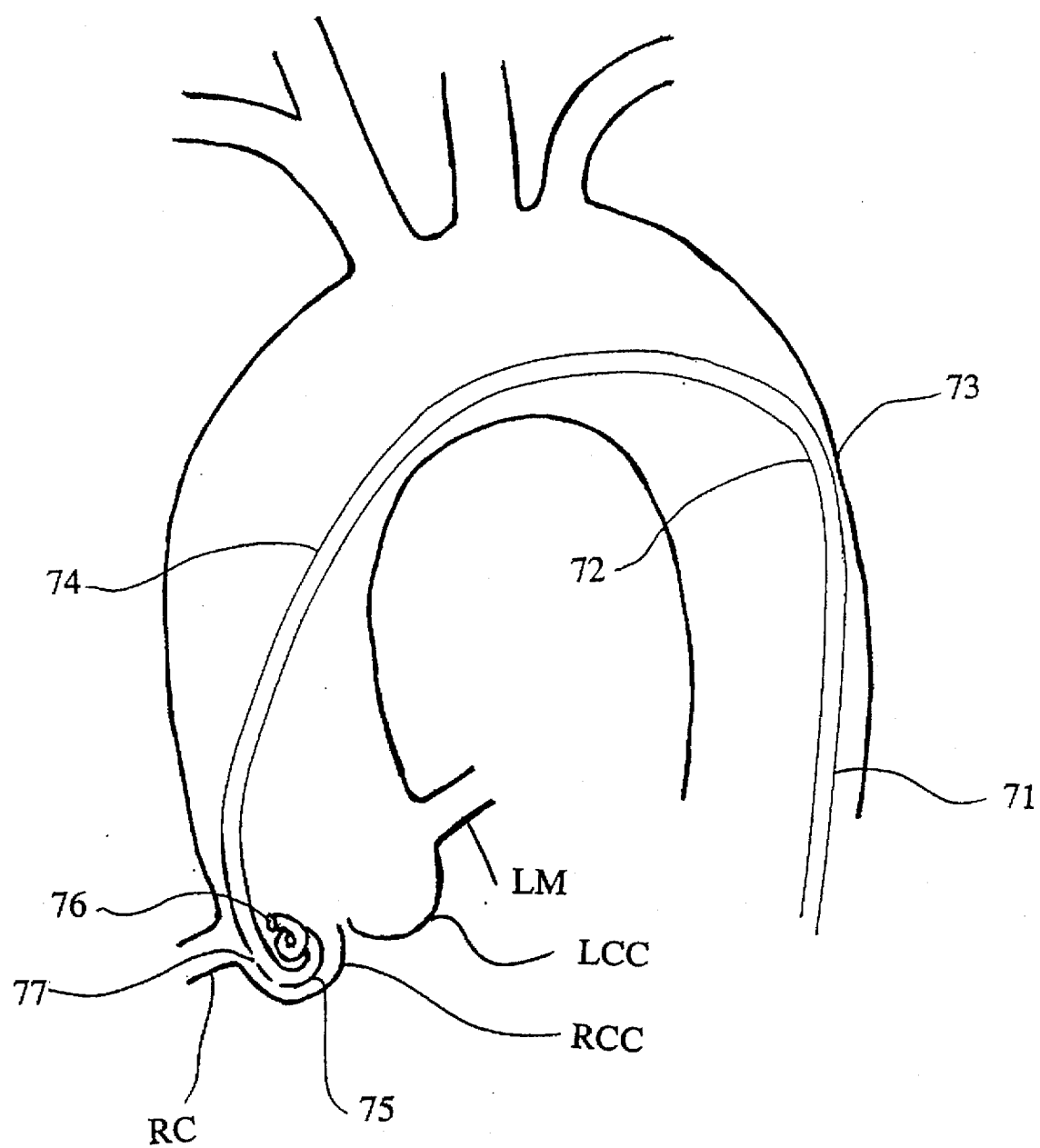

FIG. 13. Shows schematically some other details of such a catheter that is very much similar to the one shown in previous FIG. 3. Except the end piece of this unit shown at 75 has a special spiral shape (it will be somewhat similar to the shape of the body of snake, standing upright) that is designed to allow the catheter to touch the body of the aorta and to move along the side of the aorta and to slide gently to end in the right coronary cusp. The spiral shape of the tip of this catheter as shown at 75 has advantages as follows: first, it prevents the catheter to scratch the wall of the ascending aorta during the trip of the catheter toward the aortic valve area; secondly, it prevents the catheter from wedging in the opening of the coronary arteries which is an unwanted event and sometimes may be deadly; third, this curvature allows the tip of the catheter to slide easily to be located in the coronary cusps almost automatically.

The body of this catheter is designed with special curve and torque in order to allow the tip of the catheter to slide along the aorta and to end inside the right coronary cusp. The curvature 72 as well as the length of the catheter at 74 will be calculated to allow it to happen.

The end of this catheter 75 has an opening as shown at 76 as well as at numbers of the side holes. One side hole is shown at 77 which will be properly located in order to deliver the fluid to the vicinity of the right coronary. Importantly, the spatial shape of the end tip of this catheter may vary to allow spindle type or similar type end pieces to be made for the best handling and placement of this catheter in the right coronary artery cusp or in the vicinity of its opening.

Figure 14:
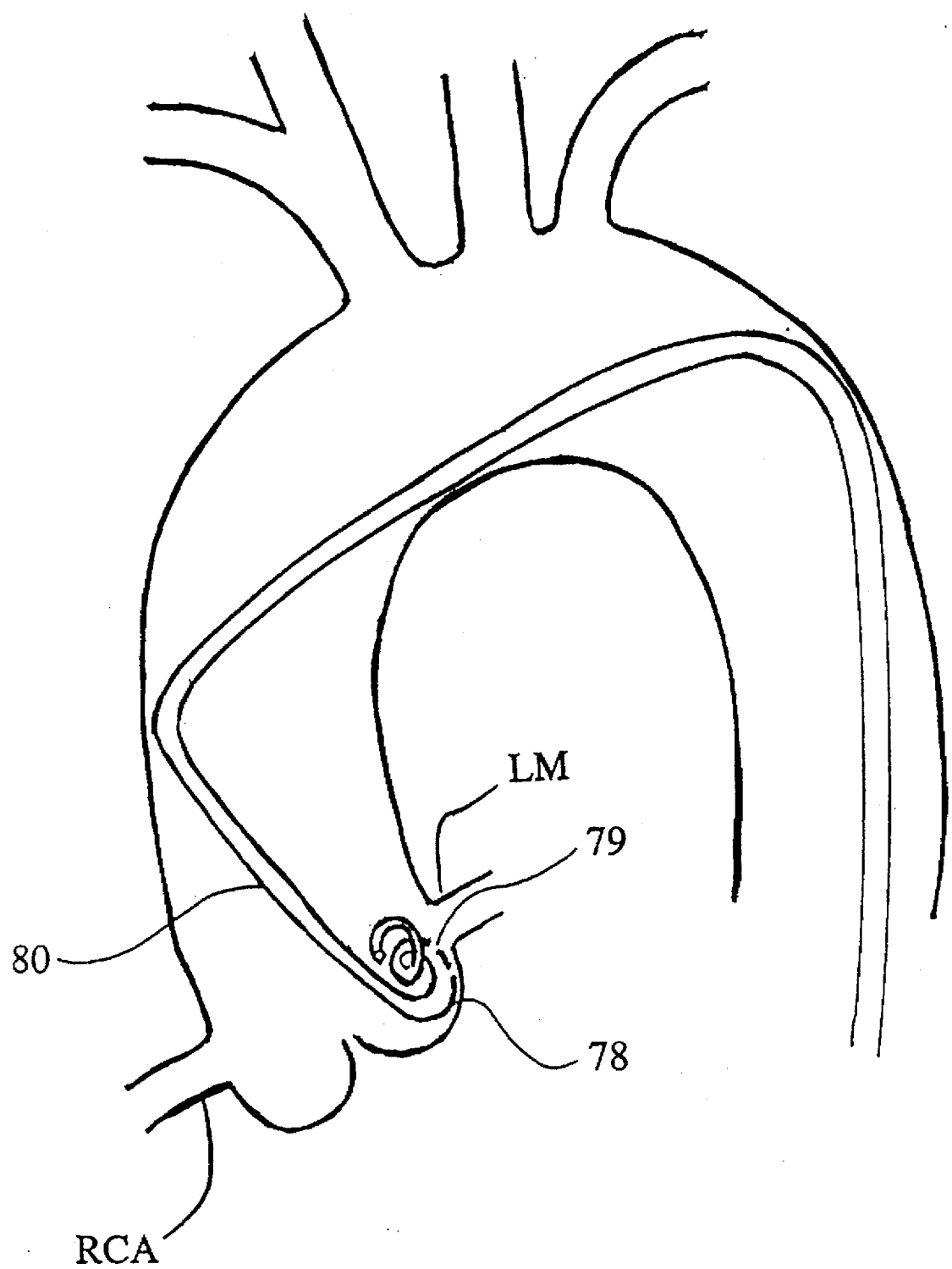

FIG. 14. Shows schematically a catheter that is very much similar to the one shown in previous FIG. 13. Except the end part of this unit shown at 78 has a spiral type shape that is designed to be placed in the left coronary cusp in the vicinity of the opening of the left main coronary artery. The spiral shape of the tip of this catheter marked at 78 prevents the catheter from scratching the wall of the aorta and it will prevent the catheter from wedging in the opening of the left main coronary artery and also facilitates the tip of the unit to slide and securely sit in the left coronary cusp. The end of this catheter may be blind or it may have an opening as well as some numbers of side holes (one shown at 79) which are placed to deliver the fluid to the vicinity of the left main coronary artery. The length of the segment 80 will vary in different sizes.

Importantly, the shape of the tip of the catheter may vary; it may have a shape more like a spindle rather than a flat base, and the size and shape of the curvature, the number and the locations of the openings and the other important characteristics of these catheters may vary to allow spindle type or similar type end pieces to be made for the best handling and placement of this catheter in the left coronary artery cusp or in the vicinity of their openings. Also importantly, the curvature of these catheters may vary in order to allow them to predictably end in the area which they are designed to end. The available science of manufacturing these catheters will be used for such purpose.

FIG. 15 schematically shows a model of the unit similar to one shown in the previous FIG. 1 except the body of the sheath of this unit is very much similar to the commonly used vascular sheaths that has been available for a long time. In this model the body of the sheath 81 has a one way valve 82 that allows the catheter to be entered however the blood would not leak out with or without the presence of the catheter. Also the body of this sheath has a tubing 83 that connects to a connection mean 84 that fits the commonly used syringes and has the valve 85 that closes it. Again these are very much the same as the vascular introducer sheaths that are available now and allows the system to be regularly flushed. Importantly, this model of sheath can be used with any of the catheters mentioned above. Importantly, cutting this unit in spots A and B will leave a balloon mean that can be attached to the body of a catheter in order to make it a balloon with a resistance. The attachment can be done by use of glues or mechanical means etc. Importantly, a unit such as the cut piece may be made to be used optionally.

FIG. 16 schematically shows the main body of an injection system that allows a calculated injection of fluid inside the catheter as well as into the balloon of the sheath mean to be done. This unit has two injection means; 87 and 88 which allow the injection of the materials into the system and into the resistant balloon 4 from FIG. 1 and 15 to be done by use of computerized pump mean shown at 86. This computerized system is schematically shown and one control button of the computer is shown at 89 and it has pump means that allows the speed, the mount and other important characteristics of this unit to be controlled.

The applicants keeps his right to file a continuation in part for such an injection unit.

Figure 17:
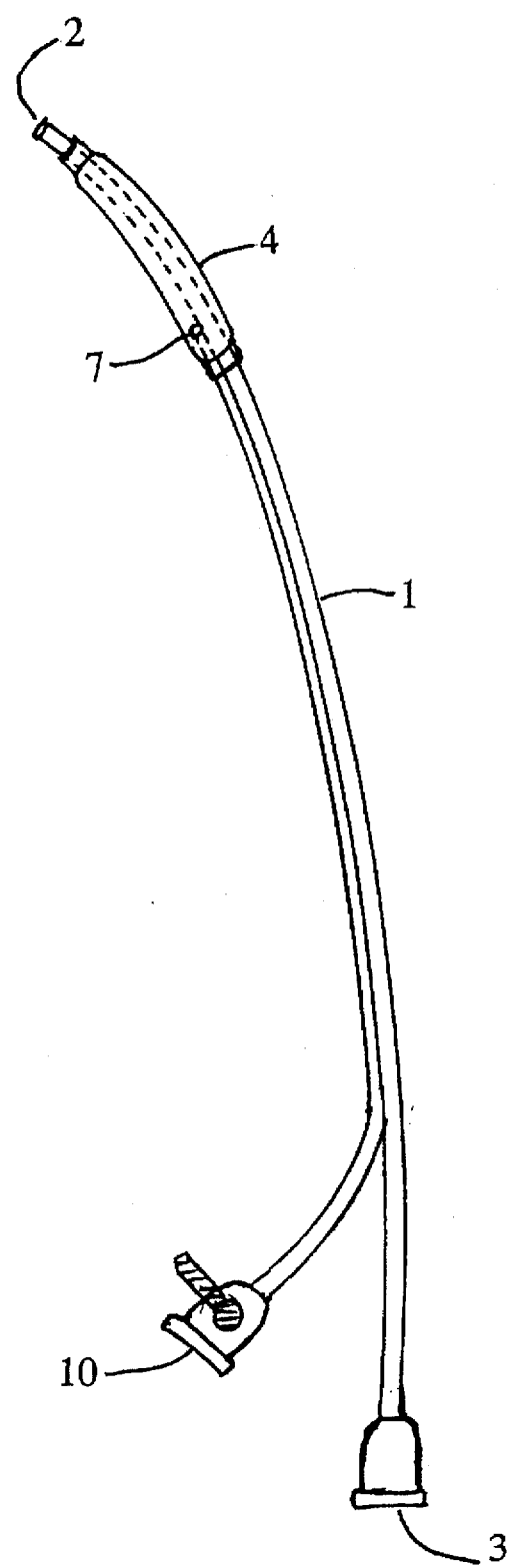
FIG. 17 shows a modified version of the unit shown at previous FIG. 1 which is to prevent from scraping of aorta during the insertion of such units.

FIG. 17 shows schematically a modified version of the unit shown at previous FIG. 1. Which is modified in order to be used during the insertion of such sheaths and other large bore catheters, guiding catheters etc to prevent the tip of such units to scratch and scrape the wall of the aorta during their placement. In this model the unit shown in the FIG. 1 is modified to have a small body to fit on the body of a commonly used guide wires so that the guidewire will fit inside the tubular lumen of this unit as shown at 2–3 in this figure and allow this unit to moved along the guidewire freely. This unit will have a small, long inflatable balloon 4 that will be sized to expand and fill up the inner lumen of the tip of the catheter or sheath that is intended to be used with. The inflation of the balloon will be done via the port 10. At the time of use this unit will be placed inside the catheter or sheath and it will be inserted into the vessel over the guidewire and then the balloon of this unit will be inflated to fill up the inner lumen of the tip of the catheter or sheath so that the tip and part of the inflated balloon of this unit will be out of the catheter and this mechanism will prevent the scraping and scratching of the wall of the aorta by the tip of the catheter or sheath. After the catheter or sheath is in place the balloon of the unit will be deflated and pulled out. Naturally the size of this unit will match the size of the catheter that it will be used and will fit inside it.

DETAILED EXPLANATION OF THIS INVENTION

The injection of a therapeutic or a procedural fluid into a vascular system and particularly into the arteries is common. One of such injections is the use of contrast media for the recognition of the anatomy of the aorta, its branches and the spaces of the heart which is referred as cardiac catheterization or angiography of a vessel or its branches. However during such an injection commonly the contrast media quickly washes out by the rapid flow of the blood and this does not give enough chance for the observer to see the details of the area. For this reason this applicant previously introduced a series of catheters that had resistance in their bodies so that these resistances prevent from the rapid washed out of the injected fluids. However since the size of the aorta is not the same in different people the applicant introduced this model that allows the place that the resistance can be placed to be chosen. This invention also allows to increase the pressure in the injected space in order to force the flow of the medication into a stenosed or occluded vessel. Furthermore the application considers introduces a series of catheters and methods that allow an easier injection of the procedural or the therapeutic materials into the culprit arteries or a space to be done. Also this application deals with the problem of measuring the blood flow in the arterial system which is very important but difficult and introduces catheters which allows such measurements to be done more accurately. Also this application also discusses a mechanism that allows a selective injection of a procedural or a therapeutic material into a main vessel to be done as well This mechanism continues the idea of use of the injection catheters which they have a resistance on their bodies and these resistances will prevent from the quick wash out and disappearance of the injected materials in the arterial system or any similar space. The prototype of such a unit was previously introduced to the USPTO by this applicant in the application of "NO-Delay Approach to Acute Medical Catastrophes, The Methods and Means". That application showed a series of injection catheters which had a resistance on their bodies such as a balloon, a wall etc. However since the use of catheters with a fixed balloon on their body may be difficult or impossible in some cases since the location of the balloon compared to the tip of the catheter can not be chanced as desired now he introduces these units to solve such a problem to a great degree. These new units consists from combination of a resistance unit such as one shown at FIG. 1 and an injection catheter FIG. 3 which can be placed in the lumen of the vessel or the ventricle of a living body independently so that this will provide a significant degree of flexibility. The combination of this model is shown at FIGS. 4 and 5. In order to show the details of each unit each one of these parts in a separate figure. FIG. 1. Shows schematically a prototype unit which has an inflatable balloon on its body for the creation of the resistance. This unit has a tubular body as shown at 1 this body has a distal opening at 2 and a proximal opening shown at 3 which allows a catheter to be placed and moved inside this tubing or a fluid to move inside this tubing for various reasons. The body of this tubing will be made from a flexible polymer which may also have a reinforcement skeleton inside its wall. The reinforcement may be made from a mesh or a skeleton of steel or a similar resistance material and it will have at least one of the following functions:

a. The reinforcement allows the shape of the unit to be preserved.
b. The reinforcement allows the unit to have a torque and to be manipulated easily.
c. The reinforcement makes the unit to resist the force which will be created during the flow of the blood that pushes the resistance away.
d. The reinforcement allows the unit to have a particular shape.

This unit has an inflatable balloon as shown schematically at 4 which is fixed to the body of the unit at point 5 and 6. This balloon has an inflation tubing such as one shown at 8 and 9 which has an opening inside the balloon as shown at 7 and an inflation port as shown at 10. The inflation port allows a syringe or an automatic injection system to be connected and used for the inflation of the balloon for the injection of a gas or a fluid. The timing and duration of the inflation and deflation of this balloon will be optional and can be decided with the use of an automatic injector, and an aspirator.

The valve mean 11 allows the inflation port to be closed.

This piece may also have an introducer and a guiding wire (both of them to be similar to the units which are now commonly and widely used during these procedures) in order to allow this unit to be inserted into a vessel and to be used as an introducer kit.

FIG. 2 shows schematically the cross cut view of the unit shown in the previous FIG. 1. Importantly, the body of the tubing in the balloon area may be made to have a smaller radius in order to prevent the outer size of the combination of the tubing plus the balloon to be larger than the outer diameter of the rest of the tubing. Also the distal tip 2 of this unit may have a trapped body to prevent from damaging of the vessel wall during the insertion period.

The unit shown at FIG. 1 may be packed with the units shown at FIG. 2A and 2B in order to allow this unit to be used as a sheath unit. FIG. 2A shows schematically a dilator probe which will be similar to a commonly used dilator piece that are used with the intra-vascular sheath units in order to be used for the dilatation of the area of the wound and the vessel. This is made from a relatively rigid polymer that has a tube body shown at DI and an internal opening shown at OP a tapered end shown at TE and a distal end shown at DE. FIG. 2B shows schematically a J shaped spring guidewire which will be very similar to commonly used J shaped guidewires that are used in order to stand inside the needle and inside the vessel to allow the dilator and the sheath unit to be placed over it. This may be packed with the units shown at FIGS. 1 and 2A. In this figure the body of the guidewire is shown at JGW and the retractable end of this unit at RE. All of these plus a needle for puncturing the vessel will be provided in a package in order to allow the insertion of the sheath to the vessel to be done by this complete unit. This package may also have the catheter shown at FIG. 3 as well.

The resistance unit shown in FIG. 1 and 2 will be used with an injection catheter. Although this catheter can be of any kind such as a right coronary catheter, left coronary catheter or a pig tail catheter however the applicant introduces a special injection catheter such as one shown at FIG. 3 which allows the cardiac output to be calculated as well. The prototype of this catheter as shown at FIG. 3. This injection catheter will have a torque-able body in order to allow it to be manipulated easily and placed in the desired area and all of these units, the body of the catheter the balloons, the resistance areas may be coated with Heparin or any other anti thrombotic agent to diminish the chance of adhering the blood particles to the body of the unit. This catheter may have different shapes, configurations or make up in its body and its tip in order to allow it to be placed easily in the desired area. Importantly, besides those properties these catheters will have a special make up by having at least one thermistors in its body in order to allow the temperature of the injected fluid inside the catheter to be verified in order to allow the computation of the flow inside the area which that fluid is injected. In this unit two of these thermistors are shown one is marked at 20 and another one at 23. These thermistors are connected to a jack symbolically shown at 22 by an electrically conductive mean such as wire 21 and 24 respectively, so that this system will allow the change in the temperature of the fluid between these two places to be computed. This information will be used to calculate the amount of the blood which goes thorough that vessel and also to calculate the cardiac output. Therefore, during one procedure and with one catheter not only injection into an area will be done but the flow of the blood can be calculated as well. Importantly, the distance between the place of thermistor and the opening which the injection will be made may vary, this may change based on further research of this model.

Importantly, the number of the thermistor and the distance between them and the opening which the injection will be made may vary as well in the prototype unit as shown at FIG. 4 the thermistor will be only one thermistor.

Alternatively, the unit may only have a proximal thermistor (or only one thermistor) shown at no 23 which will be connected to the jack 22 by the electrically conductive mean 24. In this case the temperature of the injected fluid can be checked by an independent thermometer or a temperature sensitive probe which is connected to the computer mean or by use of a similar mean as shown at 34 FIG. 4. At the time of use the catheter 14 will be placed inside the sheath unit shown at FIG. 1 and with the use of a commonly used J shaped guide wire the tip of the catheter will be placed in the proper area such as the cavity of the left ventricle or the lumen of the aorta in the area which is desked. This combination is shown in FIG. 4. In this figure a prototype balloon enhanced sheath unit similar to the model shown at FIG. 1 is placed inside the right femoral artery, RAF and its distal tip 2 is placed above the biforcation of the aorta. And an injection catheter shown at FIG. 3 which has only one thermistor shown at 23 is utilized for the injection of contrast media into the ascending aorta. The thermistor 23 will be connected to a computer system that allows the cardiac output to be measured. This computer will be properly programed in order to calculate the flow of the blood in the area. The resistant sheath in this Fig has a short length and this is chosen to indicated that the length of this unit may vary. The tip 28 of the injection catheter 26 is placed in the ascending aorta and its distal piece 27 will be connected to an injection mean such as a syringe or an automated injection machine which will be filled with contrast media. The injection into this catheter will opacify the ascending aorta which will spread to the other parts of the aorta to fill the branches of the aorta. If there was no resistance the rapid flow of the blood would have washed the contrast media from the injected space quickly however in this model the balloon 4 from the resistance unit will be also inflated on timely basis to create the resistance in the aorta. The inflation of the balloon 4 will be simultaneous or properly timed to the injection of the aorta or it will have some variation considering the timing of the injection into the aorta.

This system and the presence of the barriers will have one or more of the following benefits:

I. The barrier will function to slow down, restrict or block the passage of the blood which is mixed with a procedural or a therapeutic material. This is useful since it will allow only a small mount of the material to be injected and will minimize the cost as well as the side effects of the injected material.

II. The presence of the barrier within the injection space will make the presence of the material in the injected space longer, this will increase the presence of the injected material in the space and allow not only a small amount of the material to be used, but in some cases it will make a higher amount of a procedural or a therapeutic material to be delivered to the area and to make it more effective. This will be useful in cases which a thrombolytic material or another medication is injected into the coronaries or the branch of a vessel and the higher concentration will enhance the result of the use of that particular medication.

III. The presence of the barrier within the injection space will make the presence of the contrast media in the injected space to be longer and in more concentration, this will increase the amount of information that can be obtained after the injection of a contrast media. This will be more beneficial in case of injecting contrast media into the aortic root for evaluation of the bypass grafts. In this case the presence of the barrier will make the contrast media to move not only slowly in the area but also to stand for a longer period of time inside the vessel for a better imaging.

IV. The barrier will cause pressure in the area distal to the barrier to increase and this may have a beneficial effect in forcing the injected material such as a thrombolytic agent into the occluded vessel.

V. Very importantly, the barrier will affect the direction and flow of the blood inside the vessel which can be beneficial. For example; during the imaging the bypass grafts the resistance unit (the inflatable balloon) may be placed in the ascending aorta distal to the presumed openings of the bypass grafts so that after the injection into the space distal to the balloon, the mixture of the contrast media and the blood will be forced to move toward the periphery of the aorta; this will make the blood to move into the bypass grafts and to make them more visible since the bypass grafts are grafted to the side wall of the aorta.

VI. The presence of the resistance unit such as an inflatable balloon will allow the position of the other units such as the catheters inside the aorta to be modified which can be beneficial in certain cases.

VII. The degree of the resistance of certain barriers (such as an inflatable balloons) can be adjustable, this allow the operator to chose the degree of resistance. A smaller inflation may only create an occlusion of about 10–30% or so; in other cases the resistance may be chosen to be much higher even to occlude the area totally. The duration of the resistance can also be controlled by the period that the resistance will be in effect.

VIII. Importantly, some models of these barriers may be made to function as a screen to prevent from the passage of small particles. In such cases the body of the unit will be made from a screen as shown in FIGS. 10 and 12A and in one model it will be like an umbrella or a catcher made from an screen FIG. 10. This model will be useful to capture the embolic properties which may be released during certain conditions and interventions. In this case the resistance against the blood motion will be low and the wall of the unit will act like a fishing basket to capture the materials and allow them to be carried out from the site of approach. Spring means will be used to allow the body of the barrier to expand when it is released and prior to the release the barrier unit will be caged inside a tubing or a covering mean (please notice FIG. 9) that will allow it to be delivered to the area and then to be freed by pulling the catheter out or by pushing the unit into the delivered area.

IX. Importantly, a model of these barriers such as one shown at FIG. 1 may be made to be used as a vascular sheath in order to allow both the insertion of the catheters into the vascular system to be done and the unit also to be used as the barrier as well.

Importantly, the injection catheter 14 will also allow the flow of the blood in the aorta to be measured as well. This will be done by use of the thermistor 23 which is placed in the wall of this catheter and it will be covered either by a thin layer of polymer or will be open to the fluid via a small opening. For the measurement a computer 29 shown in this picture will be used. This computer is shown symbolically and it has the jack 30 which will connect to the jack 22 from the catheter. The computer unit will be connected to the electrical source by the jack 31. The computer has a series of indicators; one marked at 32 which will allow the variables to be seen, it also has a series of control buttons one shown at 33 that will allow information to be relayed to the computer and different functions to be controlled. The computer may also have a probe 34 in order to allow the temperature of the injection solution to be measured for calculation.

This system will allow a fluid such as saline to be injected into the left ventricle or the aorta via the tip of the catheter 14 or an opening in its site and the temperature of the diluted fluid with blood to be checked by the thermistor 23 located in the body of the catheter. So that the change of the temperature of the injected fluid will be computed by the computer in order to calculate the flow of the blood in the area and to measure the cardiac output which is very important informations for the physicians. Therefore this unit will provide the advantage that a commonly used catheter such as one shown at 14 to be used to obtain an important information such as the cardiac output of a patient to be measured during cardiac catheterization for various reasons. The computer will use a proper software to measure all the important data.

FIG. 5. Shows schematically a combination of a resistance sheath unit such as one shown at FIG. 1 which has a longer body marked at 1 and it is used in combination with a regular pig tail injection catheter. The purpose of this Fig is also to show how the length of the resistance unit may vary in order to allow the resistance unit to be placed in different areas of the aorta for different reasons to produce a predictable and controlable resistance in different spots of the aorta. In this Fig again the aorta of a living body is shown with ascending part marked at A.A., the arch at A.ARCH and the right femoral artery at RFA. The resistance unit has a long tubular body shown at 1 and its proximal end piece is again shown at 3 the body of the balloon is shown at 4 and the inflation port of the balloon is marked at 10. The distal tip of the pig tail catheter is marked at 28, its body inside the resistance unit at 26 and its proximal end at 27. The combination of these two pieces will allow the injection of the contrast media into the left ventricle or inside the lumen of the aorta to be done and then the blood mixed with the contrast media will face the resistance of the balloon in order to disperse in the area to fill the coronary arteries and the coronary bypass grafts with a fewer numbers of injections and also to provide much more detailed information than what a regular unit can provide.

The above mentioned figures are used to indicate the following important points:

1. The size, the length, the width, the thickness, the consistency, the shape, the contour, the flexibility, the torque, the material which is used to make the body and every other important characteristics of the body of the resistance unit may vary in order to allow different models to be made.
2. The size, the width, the length, the shape, thickness of the body, the consistency, the flexibility, the material used in it and every other important characteristics of the balloon of the resistance unit may vary in order to allow different models to be made.
3. The balloons of this unit may be made to have an expandable body in order to expand with the inflation or it may be made to have a pre-designed shape that will not expand or change with inflation of the pre-designed amount of the fluid.
4. The resistance of these unit may have different nature such as being in the form of a wall made from a layer of polymer or fabric, a perforated wall, a screen etc.
5. The catheters which are used with these resistance units may vary and any proper injection catheter may be used with these units.

Importantly, the barrier unit may be modified in order to have a sturdy shaft in its body and an inflatable balloon in its tip so that this unit can be placed inside the aorta next to the body of the injection catheter. An example of this model is shown at FIG. 8. This Fig shows schematically a unit that is made from a shaft 44 that has a torque-able, controlable sturdy body made from a rigid or semi rigid material such as steel wire (similar to commonly used guide wires) which may be covered by a layer of polymer) or it may be made from a somewhat rigid shaft made from a polymer that may be covered by a none or less thrombogenic polymer plus a resistance piece or a barrier part as shown at 43 which in this model is an inflatable balloon, although it can be made from other kinds of barriers such as a wall made from a layer of polymer or fabric etc. The shaft of the unit 44 has a contoured soft tip 45 in order to prevent from damaging the wall of the vessel during the insertion period (in some models this part may not exist and in another models it may have a J shaped soft tip made from a spring) also the body 44 of this unit has a torque-able, resistant, sturdy make up which allows it to be properly manipulated to be positioned inside the aorta or other vessels of a living body (the degree of the torque-ability and the resistance of the body will vary). The body 44 of this unit has a tubular make up with a proximal opening 46 that allows the balloon to be inflated. A valve mean allows the balloon to be kept inflated. This unit can be placed inside the aorta next to an injection catheter in order to create a controlable resistance inside the lumen of the aorta and to function similar to the unit explained in the text. It is important to notice that the reason for sturdy construction of the shaft of this unit is that otherwise the rush of blood in arterial system will simply push the resistance away and prevent from functioning of this unit.

Importantly, this unit may also have a tubing similar to the tubing 40 from the previous FIG. 7 to be used for purposes such as injection of the fluids into the lumen of the vessel or for the measurements of the pressure of the space distal to resistance. Also importantly this tubing will allow a guidewire to be entered into it in order to keep the unit in place securely during the inflation period and prevent it to coil.

Also importantly, the balloon can be made to be part of the injection catheter this was previously mentioned in the application of this applicant in "No delay approach to acute vascular catastrophes" and a model of such a unit is shown in this application in FIG. 6. This figure shows schematically a pig tail injection catheter which also has a resistance unit such as an inflatable balloon as part of its body. The injection catheter will be made to be similar to a high quality injection catheter that is available now for this purpose; such as a commonly used pig tail catheter as shown here at 35. However the body of this unit is further modified with placement of an inflatable balloon such as one shown at 36 also it will be more intensified in order to be able to resist against the pressure of the blood when the balloon is inflated. This balloon has an inflation tubing 37 and an inflation port 38 so that it will allow the balloon to be inflated when the catheter is in a proper place to be functional. The proximal end of this catheter is shown at 39.

This method and mechanism allows catheters with different shapes to be made with different sizes and the resistance bodies such as balloons to be mounted on different areas of them to be available for use in particular sizes and cases. This catheter will function similar to the prototype unit mentioned in this text except the position of the balloon in the catheter will be fixed.

Importantly, the balloon or the resistance of these unit may be made to slide on the catheter and to be placed on a proper area of the catheter prior to use. In this model the balloon will have a tubing in its center that allows the balloon to be created and to move along the length of the catheter. Such a resistance units may be fixed on the body of the catheter by use of glues, snaps and similar means.

FIG. 7. shows schematically a unit which is similar to the previous FIG. 6 except it also has an extra tubing which allows the pressure of the area distal to the balloon to be measured. In this Fig the body of the catheter is shown at 35 and has the resistance unit symbolically shown as an inflatable balloon (it can be other kinds as well) at 36. This unit has the tubing 40 which has a distal opening 42 and a proximal opening 41 that allows it to be used for various reasons such as the injection of fluids to the area or for measurements of the pressure of the area distal to the resistance.

Importantly, although all these units allow the main goal of this application to be achieved however the unit shown at FIGS. 1 and 8 have the advantage that they allow different size catheters to be used with them and the position of the resistant unit inside the aorta to be chosen which is an important issue. Otherwise different sized catheters with a resistance on them have to be made to be used in different persons of different sizes.

Also importantly, the shape of the tip of the injection catheter and is body may also vary as well. The catheter may have a tip with the following characteristics:

m. The catheter may have a pig tail shaped tip for general injection.
n. The catheter may have a proper curvature with an open tip to allow it to be placed in the opening of a particular coronary artery.
o. The catheter may have a spindle shape tip such as commonly used coronary injection catheters to allow the catheter to be placed in the opening of a particular coronary artery.
p. The tip of the catheter may have any other possible shape that can be used with this system.

Also importantly, the make up, the shape, the size, curvature, torque-ability, thickness, relative sizes of their components and all other important characteristics of the body of these catheters may also vary in order to allow the following goals to be achieved.

s. The catheter may have a body and a pig tail to allow it to be placed in the ventricle or the center of the aorta. These catheters will be designed with use of the present knowledge so that the tip of the catheter to move along the body of the aorta and to stand about the center of the aorta.
t. The catheter may have a body to allow it to be placed in the right coronary cusp of a living body in order to allow the injection of a procedural or a therapeutic fluids in this. In this model the curvature and the torque of the body of the catheter will be designed to be similar to the present right coronary catheters so that the tip of the catheter to move along the body of the aorta and to stand in the right coronary cusp.
u. The catheter may have a body to allow it to be placed in the left coronary cusp of a living body in order to allow the injection of the a procedural or a therapeutic fluids in this area to be done. In this model the curvature and the torque of the body of the catheter will be designed to be similar to the present left coronary catheters to allow the tip of the catheter to move along the body of the aorta and to stand in the left coronary cusp.

Basically this catheter will be made to be similar to the body of commonly used high quality cardiac catheters that are now being used for the injections into the ventricles, and are mainly made from a skeleton that is made from metal or a tubular flexible metal screen covered by a polymer. Such catheters are made now for the coronary arteries, the carotid arteries, the renal arteries and some other particular areas. These catheters have a torque-able body and they will have a surface coating made from Heparin or any other similar anti thrombotic agent to diminish the chance of the blood particles to adhere to the surface of these catheters. This catheters may have different shapes, curvature and design.

The rule of the barrier: Importantly, these catheters may have other means of producing a barrier or a resistance against the movement of the blood. This may be done by means such as the use of an inflatable balloon as mentioned or it may be made to be a wall; similar to the body of an umbrella that will expand after being released from a delivery cover in order to stand against the movement of the blood. In this model the barrier will be located on the body of the unit as shown in FIG. 9. These barriers may be made to be used in any location of the catheter; such as inside the ventricle, in the ascending aorta, in the aortic arch, in the descending aorta or in the branches of the aorta depending to the purpose of the use of the barrier. In some models they may be chosen to be in the proximal area and in some to be distal depending on the purpose of use of these units. Importantly, the barrier may be placed in the distal aorta prior to the bifurcation of the aorta in order to prevent from displacement of the unit due to the force of the incoming blood. Many of these aspects were discussed in the previous application of this applicant however the main advantage of these new units is that they allow the position of the barrier on the catheter to be changed and adjusted. The benefits of the use of barriers was discussed above.

The properties of the barriers.

The barriers may be made to from different properties; one is the use of an inflatable balloon which will have an inflation port. This part will be placed in the proximal area of the injection site in arterial system and such a placement will allow the balloon to be inflated by injection of a fluid and the inflated balloon will create the resistance. The body of this balloon may be made in different ways:

a1. In this model the balloon will be made to have an expandable body so that with the inflation of the balloon or the injection of the fluid inside the balloon its wall will expand depending on the volume of the injected material so that finally it will totally occupy the area.
a2. The balloon may be made to have a predesigned shape and size so that with inflation or injection of a predesignated amount of fluid the shape and size of the balloon would not change noticeably.
a3. In some models the unit will have a body that will function between the spectrum between those two extremes.

The balloons may have an elastic consistency in order to shrink when it is not inflated. In some models the elastic balloons may have small holes in their wall to allow the injected fluid to leak out into the area. This will allow the contrast media or the injected material to be released from the balloon while the body of the balloon and the related resistance will decrease and shrink. This combination will allow the opacification of the injected space to occur while the resistance will gradually decrease and vanish to allow the circulation to continue its normal pattern.

The position of the balloons on the body of the catheter may also be different as well, and it may be made to be adjustable so that before use of the catheter the position of the balloon on the catheter could be changed or adjusted depending on different factors such as the size of the patient. A film or a drop of adhesive may be used to fix the body of the moveable balloon on the wall of the catheter. The length, size, height, diameter, consistency and all the other characteristics of these balloons may vary to allow different units to be made.

Importantly, these units may have more than one balloon on their bodies in order to allow them to be used with different patterns of inflation and for different purposes.

The advantages of injecting a smaller amount of the procedural, or therapeutic material are as follows:

1. It will decrease the side effects of the injected materials such as the thrombolytic agents since they are mostly dose related. Therefore, the small mount of the medication can be used in cases which otherwise the use would not be justified.
2. It will decrease the side effects of the contrast agents and allow it to be used in a lesser amount in cases such as patients with renal failure, heart failure, etc., whenever the amount of these materials should be limited.
3. This method will allow the obtaining more information even with injection of lesser amount of materials such as the injection of the aortic root for visualization of the bypass grafts as mentioned above.

Importantly, the position of the barrier on the catheter may be adjustable in order to allow the position to be changed. Also, in some cases the barrier may be a totally different unit and allow it to be placed in different areas. This will allow a balloon of different size or shape to be mounted on the tubing to be used for a particular reason. In such models the body of the balloon may have an inner tubing in order to allow it to be moved along the body of the catheter.

The attachment may use different connection means such as snaps, adhesives etc.

Importantly, the size, shape and location of the balloons may vary. The balloons may have tapered ends or they may have a bulged body and a sharper side walls.

The body of the tubing of the sheath or the body of the catheter may also have another tubing in order to be used for various purposes such as to allow the pressure distal to the balloon to be checked, or a procedural or a therapeutic material to be injected to the area.

Importantly, in order to prevent the wall of the balloon from standing very close to the wall of the aorta, the outer surface of the balloon may be made to have a series of walls or protrusions which will prevent the wall of the balloon to stand substantially close to the wall of the aorta.

Importantly, the action of the effect of the shape and location of the barriers and the moving blood will be considered with a great deal of sophistication in order to allow the barrier to be made to affect the motion of the blood in the direction which is desired. The barrier may be chosen to direct blood in one direction or to prevent the blood from moving in a certain direction; this will be a very useful tool in directing the blood in different directions. The barrier may be made to be like a wall and it may be made to have different shapes, sizes, contours and other important specifics. An example of such a unit is shown at FIG. 9. This figure shows schematically a couple options that the resistance units mentioned in the above figures may have.

First. The body of the tubing of the resistance unit=the sheath or the catheter may be made to be a double lumen tubular unit marked at 48 and 49. This will allow various uses for example it will allow one lumen to be used for the injection of the fluid and the other lumen to be used for the placement of a guide wire in order to provide more stiffness and resistance to the body of the combination and to prevent the blood flow to move the resistance part away.

Second. This Fig also shows how the barrier part of the resistance unit may be made from a wall as shown in no 51. This wall may be made from a layer of polymer or a fabric that it will function such as an umbrella or a reversed umbrella in order to resist the flow of the blood. In this Fig the body of the catheter is shown at 47, one opening at 48, the other one at 49, and the dividing wall between these two long tubular openings at 50. The dish shaped, barrier is marked at 51. This figure also shows a larger catheter marked at 47A that will function to hold the unit 47 as well as the wall mean 51 inside and will allow them to be delivered to the target area. After the unit is in the proper place then the catheter 47A will be pulled back and out to release the wall mean 51. This figure also shows a string mean ST that is connected to the body of the resistance wall mean 51 in order to allow the position of the wall to be adjusted inside the body.

The other figures such as FIG. 10, 11, 11A, 12 and 12A all show other barrier means that may be made to serve the useful purpose which is explained in this text. Each one has their own specifics and introduce an important issue. In regarding the barrier means the following issues are important:

1. The size, the length, the width, the thickness, the consistency, the shape, the contour, the flexibility, the torque and every other important characteristics of the body of the above mentioned resistance units may vary in order to allow different models to be made.
2. The size, the width, the length, the shape, thickness of the body, the consistency, the flexibility and every other important characteristics of the body of the balloon of the resistance unit may vary in order to allow different models to be made.
3. The balloons of this unit may be made to have an expandable body in order to expand with the inflation or it may be made to have a pre-designed shape that will not expand or change with inflation of the pre designed mount of the fluid.
4. The resistance of these unit may have different nature such as being in the form of a wall, a perforated wall, a screen etc.
5. The catheters which are used with these resistance units may vary and a regular injection catheter may be used with these units.

Importantly, the applicant would like to mention that the resistance unit may be modified in order to have a resistant shaft in its body and an inflatable balloon in its tip so that this unit can be placed inside the aorta next to the body of the injection catheter as well. A model of this unit is shown at FIG. 9.

The units mentioned above may have one or more of the combinations of the following functions:

I. The barrier will function to slow down, restrict or block the passage of the blood which is mixed with a procedural or a therapeutic material. This function is useful since it will allow only a small mount of the material to be used to minimize the cost as well as the side effects of the material.

II. The presence of the barrier within the injection space will make the presence of the material in the injected space longer which will increase the concentration of the material in the space and allow not only a small amount of the material to be used, but also an even higher amount of the a procedural or a therapeutic material to be delivered to the area and to make it more effective.

III. The presence of the barrier within the injection space will make the presence of the contrast media in the injected space to be longer and in more concentration, this will increase the amount of the information that can be obtained after the injection of a contrast media. This will be especially true in the case of injecting contrast media into the aortic root for the evaluation of the bypass grafts. In this case the presence of the barrier will make the contrast material to move not only slowly in the area but also to stand for a longer period of time.

IV. In the arterial system such as aorta as shown in FIG. 4 and 5 the barrier will cause the pressure in the space distal to the barrier to increase and this higher pressure will have a beneficial effect in forcing the injected material such as a thrombolytic agent into the occluded vessel which is believed to have a beneficial effect.

V. In some cases the presence of the barrier will affect the direction and the motion of the blood inside the vessel such as the aorta which can be beneficial in certain cases. For example; during the evaluation of the bypass grafts the resistance may be placed in the ascending aorta so that after the injection into the distal area of the barrier the mixture of the contrast and the blood to move mostly toward the periphery of the aorta; this will make the blood to move into the bypass grafts and to make them more visible since the bypass grafts are grafted to the side walls of the aorta.

VI. Importantly, the degree of resistance of certain barriers (such as an inflatable balloons) can be adjustable this will give a choice to the operator to decide about the degree of the resistance which is desired to be used. A smaller inflation may only create an occlusion of about 10–30% or so; in other cases the resistance may be chosen to be much higher even to occlude the area totally. The duration of the resistance can also be controlled by the period that the resistance will be in effect.

VII. Importantly, these barriers may be made to function as a screen and prevent small particles from passing thorough them. In such cases the body of the unit will be made from a screen and in one model it will be like an umbrella or a catcher made from an screen. This will be useful to capture the embolic properties which may be released during certain conditions and interventions. In this case the resistance against the blood motion will be low and the wall of the unit will act like a fishing basket to capture the materials and allow them to be carried out from the site of approach. Spring means will be used to allow the body of the barrier to expand when it is released and prior to the release the barrier will be caged inside a tubing or a covering mean that will allow it to be delivered to the area and then to be freed by pulling the catheter out or by pushing the unit into the delivered area.

VIII. Importantly, a model of these barriers such as one shown at FIG. 1 may be made to be used as a vascular sheath in order to allow both the insertion of the catheters into the vascular system to be done and the unit also to be used as the barrier as well. A sample of this unit is shown at FIG. 15 and is of special interest since it allows this unit to be used as the vascular sheath and to have the resistance mean as well.

Importantly, these catheters may be made to have a shape, contour and proper sizing in order to fit in the cusp of one particular coronary artery or any other large branches of aorta in order to make a selective delivery of a procedural or a therapeutic material in that particular area or the vessel. Two of such catheters are shown in FIG. 13 and 14. Basically the FIG. 13 shows schematically the nortic artery of a human being with its major arteries; the opening of the left main coronary artery is marked at LM, and the opening of the right coronary artery at RCA. The right coronary cusp is marked at RCC and the left coronary cusp at LCC. The special catheter is inside the aorta. The body of this catheter is shown at 71 and it has a specially designed body with a curvature that makes the catheter to touch the wall of the aorta in the vicinity of those areas in order to assume its desired shape to follow the proper route as shown here and to end up in the right coronary cusp as shown. This will consist of first touching the inner wall of the aorta in the nortic arch then to touch the wall of the aorta in the arch and finally to end in the opening of the right coronary artery inside the right coronary cusp as shown. The segment shown at 72 will stand in the arch of the aorta and the segment shown at 74 will end with a shaped tip such as one shown here at 75. The length of these segments will be calculated and will be specific for certain body sizes and the anatomical variations of the human's aorta. Thus, combinations of these as well as the special spring type body of the unit and its torque will allow the tip of the catheter to enter the right coronary cusp and stand in the vicinity of the opening of the right coronary artery without a need for much of manipulations. Importantly, the knowledge of designing and making such catheters are already available and part of prior art and for that reason the applicant does not explain such a construction.

FIG. 13. Shows schematically some other details of such a catheter that is very much similar to the one shown in previous FIG. 3. Except the end piece of this unit shown at 75 has a special spiral shape (it will be somewhat similar to the shape of the body of snake, standing upright) that is designed to allow the catheter to touch the body of the aorta and to move along the side of the aorta and to slide gently to end in the right coronary cusp. The spiral shape of the tip of this catheter as shown at 75 has advantages as follows: first, it prevents the catheter to scratch the wall of the ascending aorta during the trip of the catheter toward the aortic valve area; secondly, it prevents the catheter from wedging in the opening of the coronary arteries which is an unwanted event and sometimes may be deadly; third, this curvature allows the tip of the catheter to slide easily to be located in the coronary cusps almost automatically.

The body of this catheter is designed with special curve and torque in order to allow the tip of the catheter to slide along the aorta and to end inside the right coronary cusp. The curvature 72 as well as the length of the catheter at 74 will be calculated to allow it to happen.

The end of this catheter 75 has an opening as shown at 76 as well as at numbers of the side holes. One side hole is shown at 77 which will be properly located in order to deliver the fluid to the vicinity of the right coronary. Importantly, the spatial shape of the end tip of this catheter may vary to allow spindle type or similar type end pieces to be made for the best handling and placement of this catheter in the right coronary artery cusp or in the vicinity of its opening.

FIG. 14. Shows schematically a catheter that is very much similar to the one shown in previous FIG. 13. Except the end part of this unit shown at 78 has a spiral type shape that is designed to be placed in the left coronary cusp in the vicinity of the opening of the left main coronary artery. The spiral shape of the tip of this catheter marked at 78 prevents the catheter from scratching the wall of the aorta and it will prevent the catheter from wedging in the opening of the left main coronary artery and also facilitates the tip of the unit to slide and securely sit in the left coronary cusp. The end of this catheter may be blind or it may have an opening as well as some numbers of side holes (one shown at 79) which are placed to deliver the fluid to the vicinity of the left main coronary artery. The length of the segment 80 will vary in different sizes.

Importantly, the shape of the tip of the catheter may vary; it may have a shape more like a spindle rather than a flat base, and the size and shape of the curvature, the number and the locations of the openings and the other important characteristics of these catheters may vary to allow spindle type or similar type end pieces to be made for the best handling and placement of this catheter in the left coronary artery cusp or in the vicinity of their openings.

The special make up of these units (the catheters and the sheath pieces). Importantly, in order for these units to be used in the arterial system the unit should withstand the force of rushing blood moving toward and against the barrier and forcing it away. This will be done by use of the following methods and mechanisms:

In one model the body of the catheters will be modified in order to have special properties. This is to make the body of the catheter to allow it to bend and still be manipulated inside a vessel (such as the aorta) without losing its shape. This is an important issue since without such a property of the body of the catheter the injected blood will simply push the balloon or any other resistance means and the catheter with it out of the place and this will prevent from the proper function of this catheter. In order to prevent from such an occurrence the following steps will be taken:

a. The body of these catheters or sheaths will be made from a more resistant material made from different polymers in order to make a resistant unit.

b. The body of these catheters or sheaths will be made from a more resistant material such as combination of a polymer reinforced by a metal tubing, a metal mesh mean, metal spiral mean, metal pieces or layers in order to make a resist unit. In this case at least some part of a segment of the body of this catheter may be made to be more rigid.

c. The body of the catheter or sheaths may have a rotated or a coil of steel or spring mean type property that will allow bending of the body of the catheter or the sheath to occur but not to have the length of the unit to shorten. This may be present in some areas of the catheter or sheath if not in the whole area.

d. The body of these catheters or sheaths may have a reinforcement material means, skeleton, mesh or lines made from steel or similar material which will allow the unit to be a torque-able unit and to bend inside the vessel however not to allow the length of the catheter to shorten and the catheter to bend very easily. These components may be present in some areas of the catheter or sheath but not in all areas and importantly it may be present in some areas more that the other in order to give more stiffness and body to some areas but not to the whole unit. This will be useful since for example a catheter which has a more resistant body in the proximal area of the body than the distal one will be a proper catheter to be used in these cases.

e. The body of the catheter may be made to be thicker and somewhat more resistant and torque-able.

f. The body of the catheter may be made to have more than one lumen for various reasons for example it may have at least two lumens: one to allow the injection of the materials into the system and the second one to allow a guide wire of higher resistance to be placed inside it to secure the position of the unit in place.

g. The body of the catheter may be made to have a larger lumen in order to accommodate the presence of a guidewire of higher resistance to secure the position of the unit in place and also to allow for injection of the materials as well.

h. The consistency of the body of the catheter may vary in different areas along the body of the catheter. This will allow making different units. For example, a unit may have a flexible segment in the tip area which is the distal part to allow that part to move easily in the aortic arch. However, the segment in the proximal area will be made to be more rigid and to allow for better control and manipulation and to resist against the forced blood. This will prevent the catheter from being pushed out by the force of injected blood by the ventricle.

Importantly, during the injection period the unit is to be kept in the area securely by the operator to prevent the catheter from being pushed out by the forced blood.

The length of different segments of this catheter may vary as well; the segment that is proximal to the resistance mean as well as the segment which is distal to the resistance mean, the place of the resistance mean on the catheter or the vascular sheath may all vary to allow different units for different purposes and different size patients to be made. For example in order to inject contrast media to the area of the bypass grafts the distal segment of the catheter as well as the length of the whole catheter will be calculated and the balloon will be placed to stand distal to the openings of the grafts in order to allow proper opacification of the bypass grafts to occur.

The distal end of these catheters will have an end piece similar to the body of the commonly used catheters in order to fit the tip of the commonly used injectors and standard syringes. Except the very end part of the catheter close to the distal end which may have some toughened area in order to allow easy manipulation of the catheters.

Therefore, the body of these catheters or their tubing may have different properties, resistance means, flexibility and consistency.

Also importantly, in order to prevent from the tip of these sheaths and other large bore catheters, guiding catheters to scratch the wall of the aorta during the placement this applicant introduces a modified model of the units shown in the FIG. 1 as well as model shown at FIG. 8. The unit shown at FIG. 1 can be modified to have a small body to fit on the body of a commonly used guide wire which will fit inside its tubular lumen shown at 2–3 in FIG. 17. In this model the unit shown in the FIG. 1 is modified to have a small body to fit on the body of a commonly used guide wires so that the guidewire will fit inside the tubular lumen of this unit as shown at 2–3 in this figure and allow this unit to moved along the guidewire freely. This unit will have a small, long inflatable balloon 4 that will be sized to expand and fill up the inner lumen of the tip of the catheter or sheath that is intended to be used with. The inflation of the balloon will be done via the port 10. At the time of use this unit will be placed inside the catheter or sheath and it will be inserted into the vessel over the guidewire and then its balloon will be inflated to fill up the tip of the catheter or sheath so that the tip and part of the inflated balloon will be out of the catheter and this mechanism will prevent the scraping and scratching of the wall of the aorta by the tip of the catheter or sheath. After the catheter or sheath is in place the balloon of the unit will be deflated and pulled out.

Another model will be similar to the model shown at FIG. 8 except in this model the tip 45 of this unit will be a j shape soft guidewire and the balloon 43 will be a soft thin balloon that will match the size of the catheter and sheath and the body 44 will be similar to the body of a guidewire to allow it to be placed inside the sheath or catheter. At the time of use this unit will be placed inside the catheter and its balloon will be inflated to give a curved edge and prevent it to scratch the body of the aorta after placement of the catheter or sheath this piece will be move out and the rest of the procedure will be continued.

Importantly, the size, shape, length, thickness, material, consistency of the parts of these units, their components, the location and position of their components and every other important characteristics of these units may vary to make different units for different purposes with use of the informations in this applications.

What is claimed:

1. A device for injection of fluid into a vascular system of a living being comprising:

a first member having a distal end portion for placement in a vessel of a vascular system and a proximal end portion that remains outside of a vessel when the distal end portion is placed in a vessel;

a restrictor for restricting the flow of blood through a vessel when placed in a vessel;

a second member comprising a fluid lumen having a distal end portion for placement in a vessel of a vascular system and a proximal end portion that remains outside of a vessel when the distal end portion is placed in a vessel, said lumen having an entrance at its proximal end portion through which fluid is injected into the lumen, and said lumen having an exit at its distal end portion for discharging injected fluid into a vessel at a location that is distal to the restrictor.

2. A device as set forth in claim 1 in which said first member comprises a sheath having a guide lumen that has an entrance and an exit, and said second member passes through said guide lumen.

3. A device as set forth in claim 2 in which said restrictor comprises an inflatable balloon on the exterior of said first member and an inflation tureen extending from said balloon to a proximal end that is external to a vessel to provide for setting desired inflation of the balloon.

4. A device as set forth in claim 1 in which said first member comprises a lumen extending through the member's proximal and distal end portions, and including a one-way valve at the first member's proximal end portion.

5. A device as set forth in claim 4 including a tube that connects to the first member's proximal end portion to communicate with the first member's lumen at a location distal to said one-way valve, and another valve for opening and closing said tube.

6. A device as set forth in claim 1 including a third member comprising a fluid lumen having a distal end portion for placement in a vessel of a vascular system and a proximal end portion that remains outside of a vessel when the distal end portion is placed in a vessel, said third member's lumen having an entrance at its proximal end portion through which fluid is injected into the third member's lumen, and said third member's lumen having an exit at its distal end portion for discharging injected fluid into a vessel.

7. A device as set forth in claim 1 in which said first member comprises a sheath having a guide lumen that has an entrance and an exit, and said second member is a coronary catheter having a steerable distal end portion including a curved section for seating in a coronary cusp so that the exit of the second member will be placed proximate an opening of a coronary artery.

8. A device as set forth in claim 7 in which said second member's distal end portion has a pig-tail shape containing said second member's exit.

9. A device as set forth in claim 1 in which said first member comprises a sheath having a guide lumen that has an entrance and an exit, and said second member is a catheter having a steerable distal end portion that allows the exit of the second member to be placed proximate an opening of a branch of an aortic artery.

10. A device as set forth in claim 1 including at least one thermistor to allow the temperature in the vicinity of the device to be measured and provided as an input for computation of vascular system flow.

11. A device as set forth in claim 10 wherein the thermistor is placed in the vicinity of the proximal end portion of the second member.

12. A device as set forth in claim 11 in which there are two thermistors, one placed proximal to the other in order to allow computation of the movement or the volume of the fluid inside a vessel.

13. A device as set forth in claim 10 wherein the thermistor is placed in the vicinity of the distal end portion of the second member.

14. A device as set forth in claim 1 including a third member comprising a lumen to allow communication between a location proximal to the restrictor and a location external to a vessel.

15. A method of injecting fluid into a vascular system using a device as set forth in claim 1 wherein the first member is placed in a vessel of a vascular system and the proximal end portion remains outside of the vessel, said restrictor restricts the flow of blood through the vessel, and fluid is injected into the lumen of the second member and discharged into the vessel at a location that is distal to the restrictor.

16. A method of injecting fluid into a vascular system using a device as set forth in claim 2 wherein the distal end portion of the sheath is placed in a vessel of a vascular system and the proximal end portion of the sheath remains outside of the vessel, said second member is passed through the sheath and the restrictor is operated to restrict the flow of blood through the vessel, and fluid is injected into the lumen of the second member and discharged into the vessel at a location that is distal to the restrictor.

17. An injection catheter system for injection of fluid to a vessel of a living being comprising:

an injection catheter having a proximal end and a distal end;

at least one thermistor on said catheter to allow the flow of fluid in a vessel to be calculated; and a restrictor disposed in association with the catheter to allow a restriction to develop in the lumen of a vessel and the restriction to be changed; and wherein the thermistor is disposed on the catheter distal to the restrictor.

18. An injection catheter system as set forth in claim 17 including a tube providing communication between locations distal and proximal to the restrictor.

19. An injection catheter system as set forth in claim 17 in which said restrictor comprises an inflatable balloon.

20. An injection catheter system as set forth in claim 17 in which said restrictor is disposed on a sheath through which the catheter passes.

* * * * *